US010869603B2

(12) United States Patent
Millett et al.

(10) Patent No.: US 10,869,603 B2
(45) Date of Patent: Dec. 22, 2020

(54) DISPLAY CONTROL FOR A MULTI-SENSOR MEDICAL DEVICE

(71) Applicant: Volcano Corporation, San Diego, CA (US)

(72) Inventors: Bret C. Millett, Folsom, CA (US); Paul Michael Hoseit, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 474 days.

(21) Appl. No.: 14/133,394

(22) Filed: Dec. 18, 2013

(65) Prior Publication Data

US 2014/0180087 A1   Jun. 26, 2014

Related U.S. Application Data

(60) Provisional application No. 61/745,514, filed on Dec. 21, 2012.

(51) Int. Cl.
*A61B 5/00* (2006.01)
*A61B 8/08* (2006.01)
(Continued)

(52) U.S. Cl.
CPC .......... *A61B 5/0035* (2013.01); *A61B 5/0084* (2013.01); *A61B 5/02007* (2013.01);
(Continued)

(58) Field of Classification Search
CPC ... A61B 5/743; A61B 5/0035; A61B 5/02158; A61B 5/6852; A61B 5/6876; A61B 8/4416; A61B 8/565
See application file for complete search history.

(56) References Cited

U.S. PATENT DOCUMENTS 6,659,957 B1 * 12/2003 Vardi ................... A61B 5/0095
600/467
7,134,994 B2   11/2006 Alpert
(Continued)

FOREIGN PATENT DOCUMENTS

WO   WO 2012/138874 A2   10/2012
WO   WO 2012/154335 A2   11/2012

OTHER PUBLICATIONS

International Search Report and Written Opinion received in Patent Cooperation Treaty Application No. PCT/US2013/075710, dated Apr. 14, 2014, 14 pages.
(Continued)

*Primary Examiner* — Amanda Lauritzen Moher
*Assistant Examiner* — Katherine M McDonald

(57) ABSTRACT

Systems and methods for user control over the acquisition, processing, and presentation of medical data are provided. Some embodiments are particularly directed to controlling the display of multi-modality medical data in a multi-modality processing system. In one embodiment, a medical imaging system receives a set of medical data including a first data subset collected using a first sensor and a second data subset collected using a second sensor, where the first sensor and the second sensor are different. A display attribute to be applied to the first data subset independent of the second data subset is received. An instruction is generated that affects the processing of the first data subset based on the display attribute. The first data subset is processed according to the instruction. The processed first data subset is displayed according to the display attribute, and the second data subset is displayed independent of the display attribute.

15 Claims, 16 Drawing Sheets

(51) Int. Cl.
  *A61B 8/00* (2006.01)
  *A61B 8/12* (2006.01)
  *A61B 5/0215* (2006.01)
  *A61B 5/02* (2006.01)
(52) U.S. Cl.
  CPC ........ *A61B 5/02158* (2013.01); *A61B 5/6852* (2013.01); *A61B 5/6876* (2013.01); *A61B 5/743* (2013.01); *A61B 8/12* (2013.01); *A61B 8/4416* (2013.01); *A61B 8/565* (2013.01); *A61B 5/0066* (2013.01); *A61B 5/0095* (2013.01); *A61B 8/0833* (2013.01); *A61B 8/0891* (2013.01); *A61B 8/445* (2013.01); *A61B 8/488* (2013.01); *A61B 2562/0204* (2013.01); *A61B 2562/043* (2013.01)

(56) References Cited

U.S. PATENT DOCUMENTS

| | | |
|---|---|---|
| 8,219,181 B2 | 7/2012 | Hall et al. |
| 8,275,447 B2 | 9/2012 | Mikami |
| 8,285,083 B2 | 10/2012 | Canessa et al. |
| 2007/0016072 A1 | 1/2007 | Grunwald et al. |
| 2008/0037850 A1* | 2/2008 | Assmann .............. G06T 7/0012 382/131 |
| 2008/0269572 A1 | 10/2008 | Kanz et al. |
| 2008/0306766 A1 | 12/2008 | Ozeki |
| 2010/0130874 A1 | 5/2010 | Joeken |
| 2010/0138239 A1 | 6/2010 | Reicher et al. |
| 2010/0179434 A1 | 7/2010 | Thornton |
| 2012/0220837 A1 | 8/2012 | Alpert et al. |
| 2012/0271168 A1* | 10/2012 | Radojicic ............ A61M 5/1723 600/439 |
| 2012/0275677 A1* | 11/2012 | Bower ................. G06F 19/321 382/131 |

OTHER PUBLICATIONS

International Searching Authority/European Patent Office, "Communication—Supplementary European Search Report," for European Application No. 13864948.8, dated Aug. 5, 2016, 8 pages.

* cited by examiner

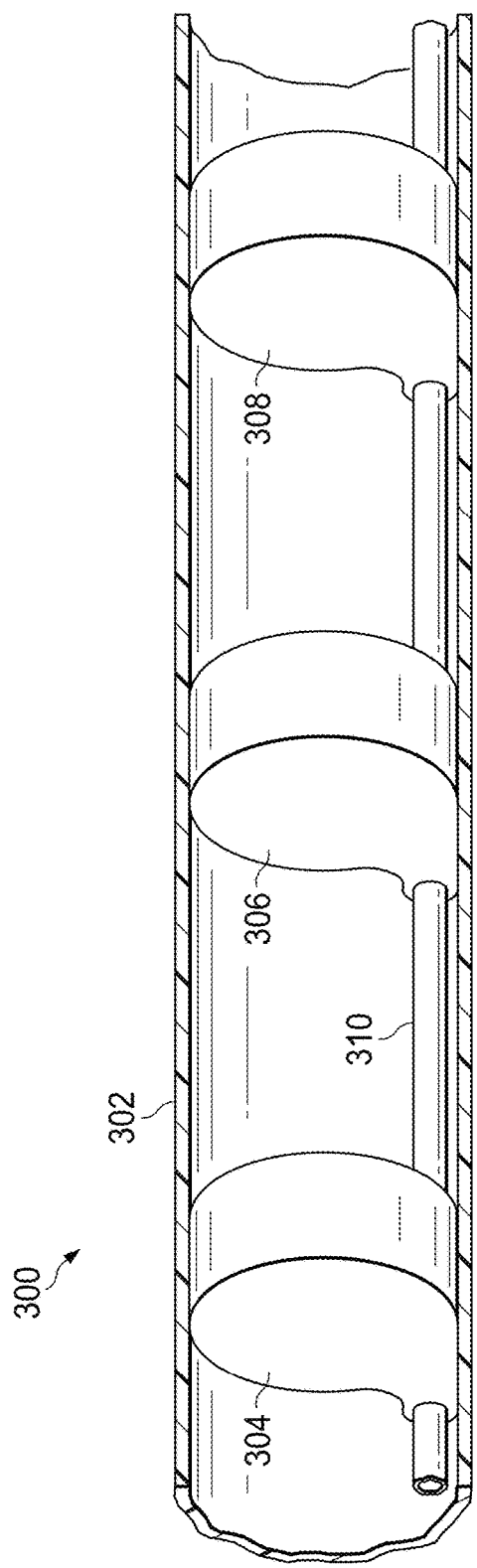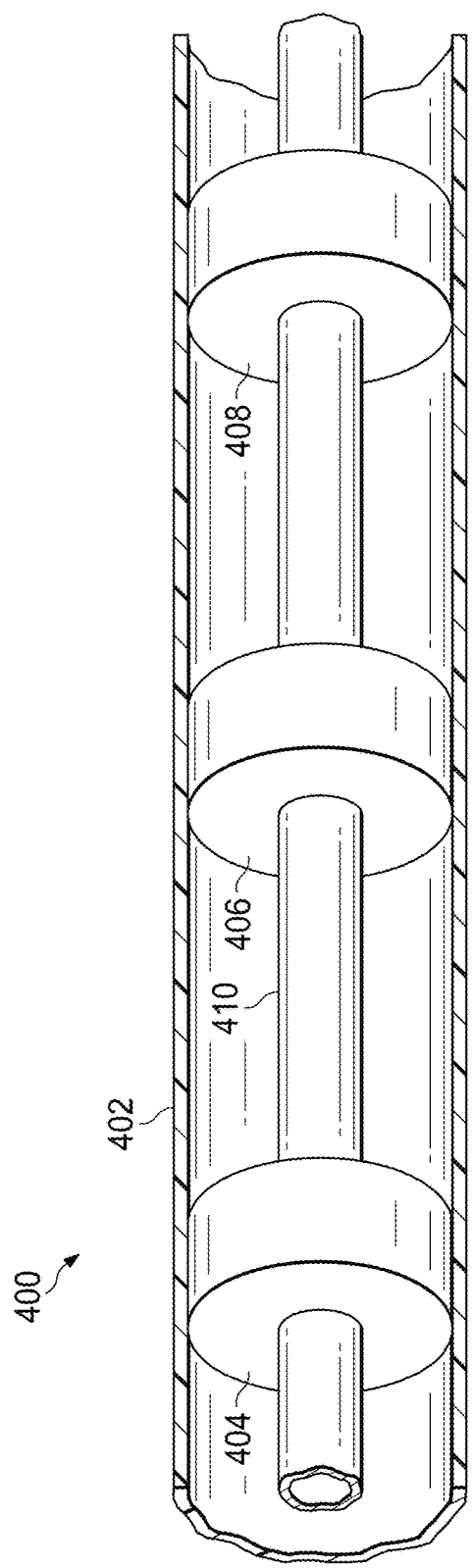

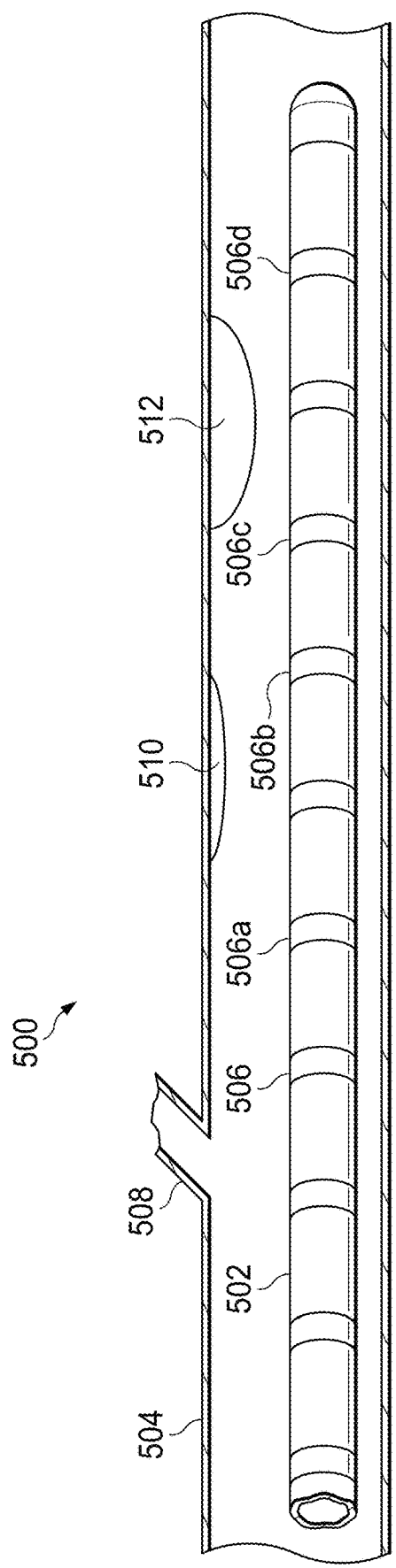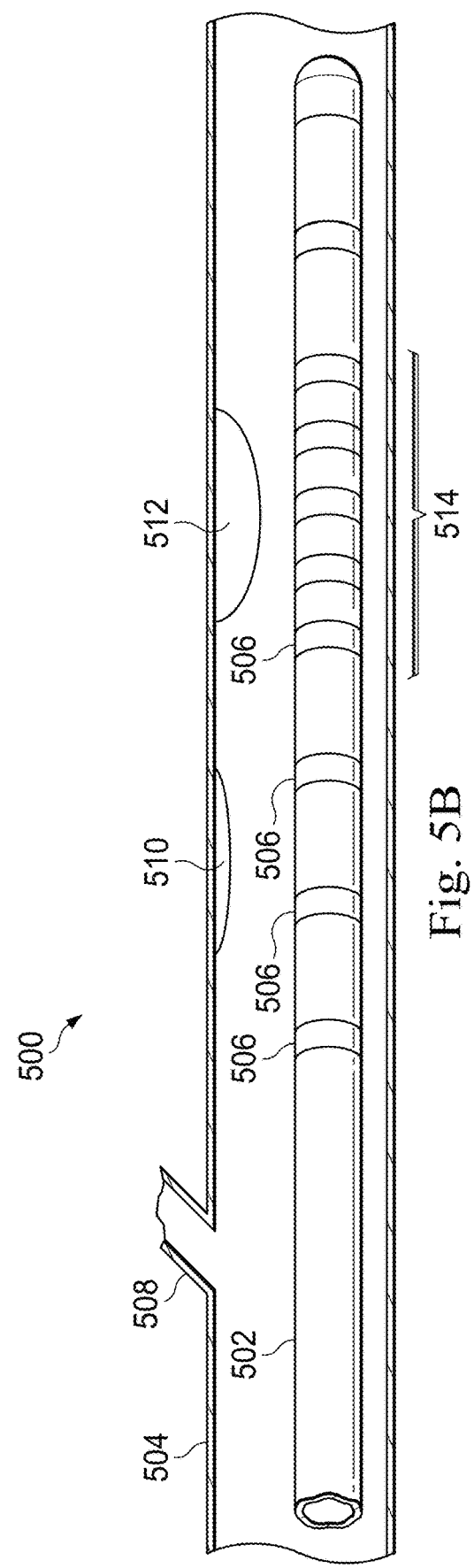

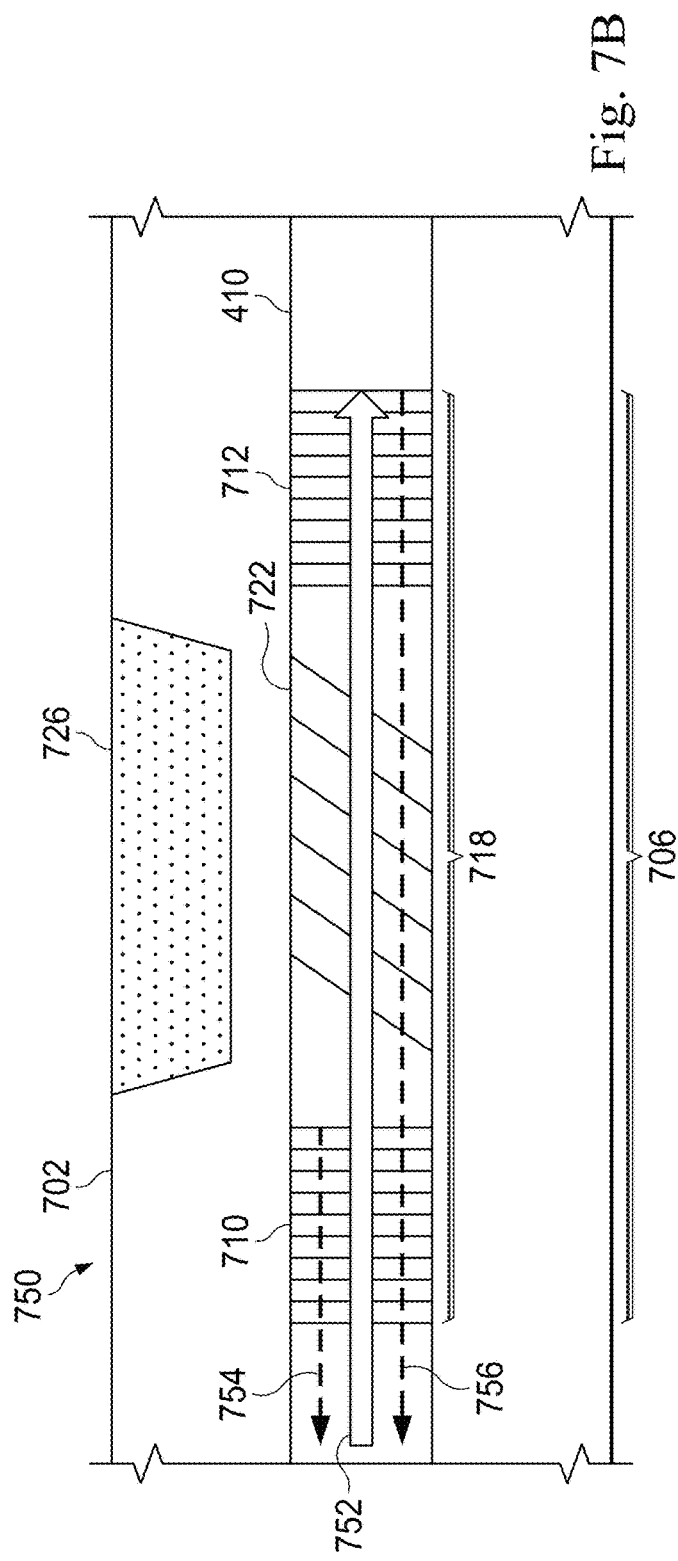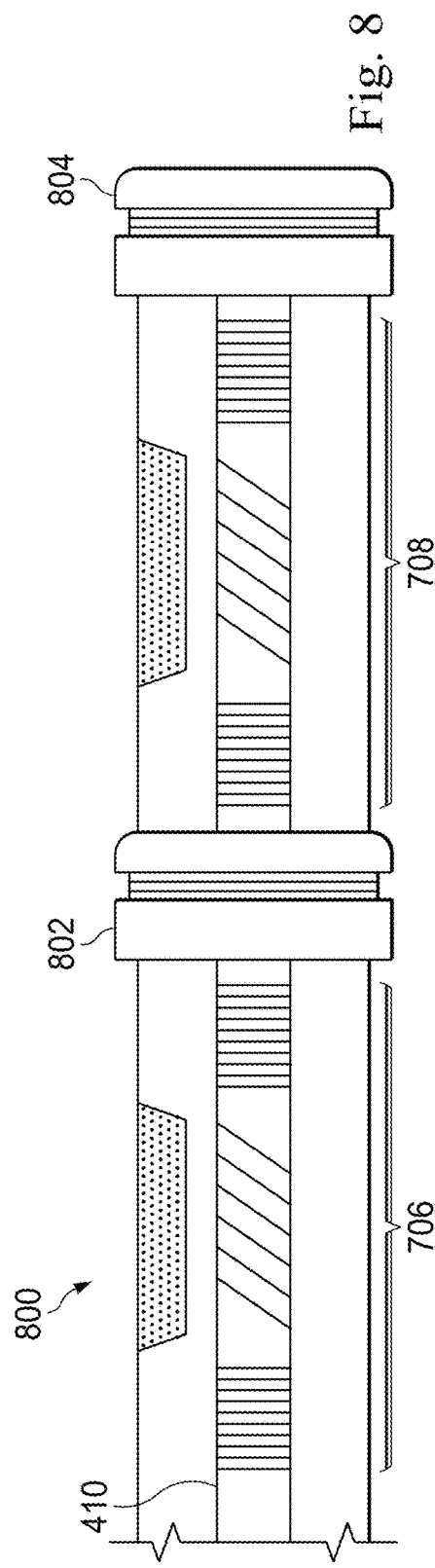

DISPLAY CONTROL FOR A MULTI-SENSOR MEDICAL DEVICE

CROSS-REFERENCE TO RELATED APPLICATIONS

The present application claims priority to and the benefit of U.S. Provisional Patent Application No. 61/745,514, filed Dec. 21, 2012, which is hereby incorporated by reference in its entirety.

TECHNICAL FIELD

The present disclosure relates generally to the field of medical devices and, more particularly, to user customization and control of the display of multi-modality medical sensing data.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. Recently, processing systems have been designed that collect medical data from a plurality of different imaging, treatment, diagnostic, and sensing tools and process the multi-modality medical data. Such multi-component systems place a wealth of medical information at the operator's command.

While existing multi-modality medical processing systems have proved useful, as the amount of information collected and processed by such systems grows, there is a direct increase in display clutter and distractions in the surgical suite. Accordingly, it becomes increasingly important to provide mechanisms by which operators may distill the collected data in order to view the most relevant portions. Improvements in display customization may enhance the operator's ability to recognize, separate, and measure relevant data. Improvements in presenting data collected across modalities in a unified, coherent fashion may also allow physicians to draw more accurate diagnostic conclusions. Thus, while existing systems have proved useful, there remains a need for greater control over the amount of data presented to the operator and for greater control over how it is presented.

SUMMARY

Embodiments of the present disclosure provide an enhanced system and method for user customization of the display of medical data in both dedicated imaging systems and multi-modality imaging systems.

The systems and methods of the present disclosure provide a mechanism for user control over the acquisition, processing, and presentation of medical data in multi-sensor and multi-modality environments. The user may specify display attributes for all or portions of a medical data set and the imaging system, based on the attributes, controls the acquisition, processing, and/or presentation of the associated medical data. This allows the user to zero in on relevant data, to improve the quality of displayed data, and to reduce screen clutter. The imaging system may also conserve system resources by selectively processing only the data selected for display. Of course, it is understood that these advantages are merely exemplary, and no particular advantage is required for any particular embodiment.

In some embodiments, a method for of displaying a set of medical data by a medical imaging system is provided. The medical imaging system receives the set of medical data including a first data subset collected using a first sensor and a second data subset collected using a second sensor, where the first sensor and the second sensor are different. A display attribute to be applied to the first data subset independent of the second data subset is received. The medical imaging system generates an instruction that affects the processing of the first data subset based on the display attribute. The instruction is provided for use in processing the first data subset. An updated first data subset is received where the updated first data subset is the result of processing the first data subset utilizing the provided instruction. The medical imaging system displays the updated first data subset according to the display attribute and displays the second data subset independent of the display attribute.

In some embodiments, a method of collecting a set of medical data by a medical imaging system is provided. The method comprises receiving, by the medical imaging system, a display attribute of a first data subset of the set of medical data. The first data subset of the set of medical data is collected using a first sensor. An instruction to collect the first data subset according to the display attribute is provided, and an instruction to collect a second data subset of the set of medical data is provided. The second data subset is collected using a second sensor different from the first sensor, and the second data subset is collected independent of the display attribute. The medical imaging system receives the set of medical data collected according to the display attribute and displays the set of medical data according to the display attribute.

In some embodiments, a method of performing tissue characterization by a medical imaging system is provided. The method comprises receiving, by the medical imaging system, a set of medical data. The medical imaging system also receives a display attribute pertaining to a tissue characterization process. The medical imaging system generates an instruction that affects the tissue characterization process based on the display attribute. The tissue characterization process is performed on the set of medical data to determine a constituent tissue element and assign a tissue identifier to the constituent tissue element. The tissue characterization process utilizes the generated instruction. The medical imaging system displays the set of medical data and the tissue identifier according to the display attribute. In some such embodiments, the display attribute includes at least one of a threshold value, a pseudo-color conversion scheme, and a display state from the group consisting of a shown state, a dimmed state, and a hidden state.

Additional aspects, features, and advantages of the present disclosure will become apparent from the following detailed description.

BRIEF DESCRIPTION OF THE DRAWINGS

FIG. 1A is illustrative of the medical system in a catheterization procedure according to some embodiments of the present disclosure. FIG. 1B is illustrative of the medical system in a cardiac catheterization procedure according to some embodiments of the present disclosure. FIG. 1C is illustrative of the medical system in a renal catheterization procedure according to some embodiments of the present disclosure.

FIG. 3 is a diagrammatic schematic view of a portion of a medical sensing system according to some embodiments of the present disclosure.

FIG. 4 is a diagrammatic schematic view of a portion of an optical sensing system according to some embodiments of the present disclosure.

FIGS. 5A and 5B are diagrammatic schematic views of a medical sensing device used in a catheterization procedure according to some embodiments of the present disclosure.

FIG. 7B is a diagrammatic schematic view of a portion of a photoacoustic IVUS system in a receive mode according to some embodiments of the present disclosure.

FIG. 8 is a diagrammatic schematic view of a portion of a multi-modality optical system according to some embodiments of the present disclosure.

DETAILED DESCRIPTION

Figure 1A:
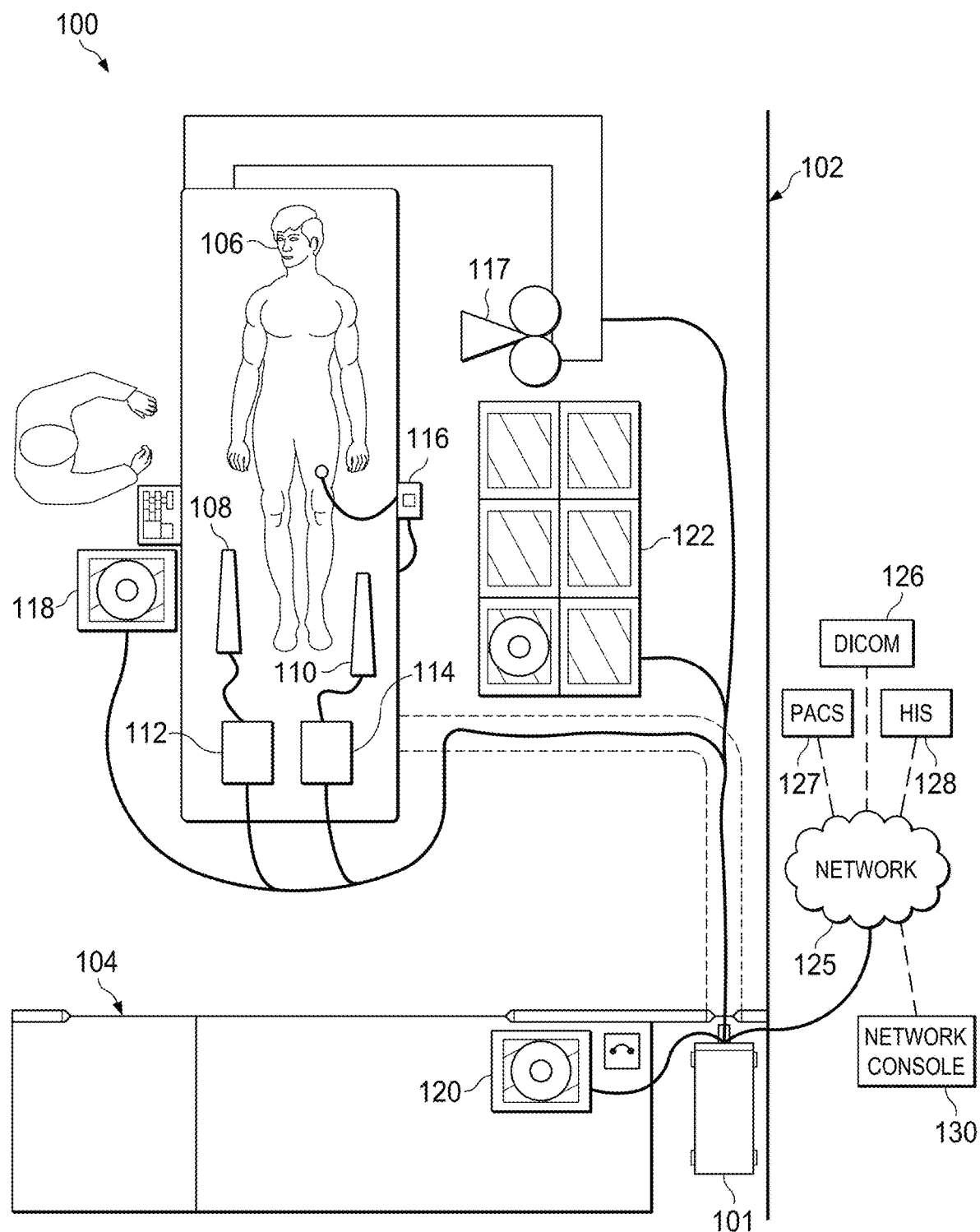
FIGS. 1A, 1B, and 1C are schematic drawings depicting a medical system including an invasive intravascular system in various applications according to some embodiments of the present disclosure. In particular.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1B:
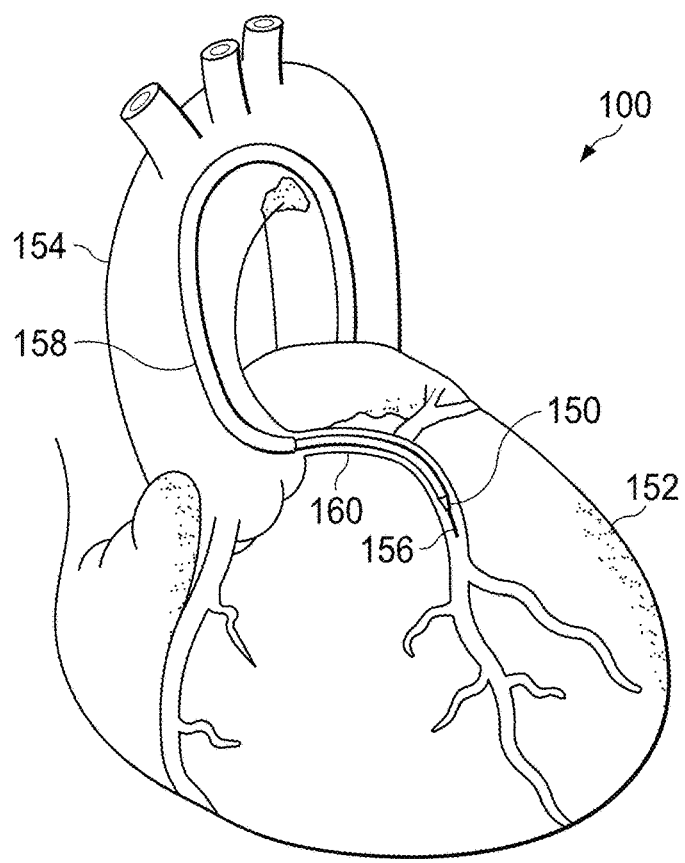
Figure 1C:
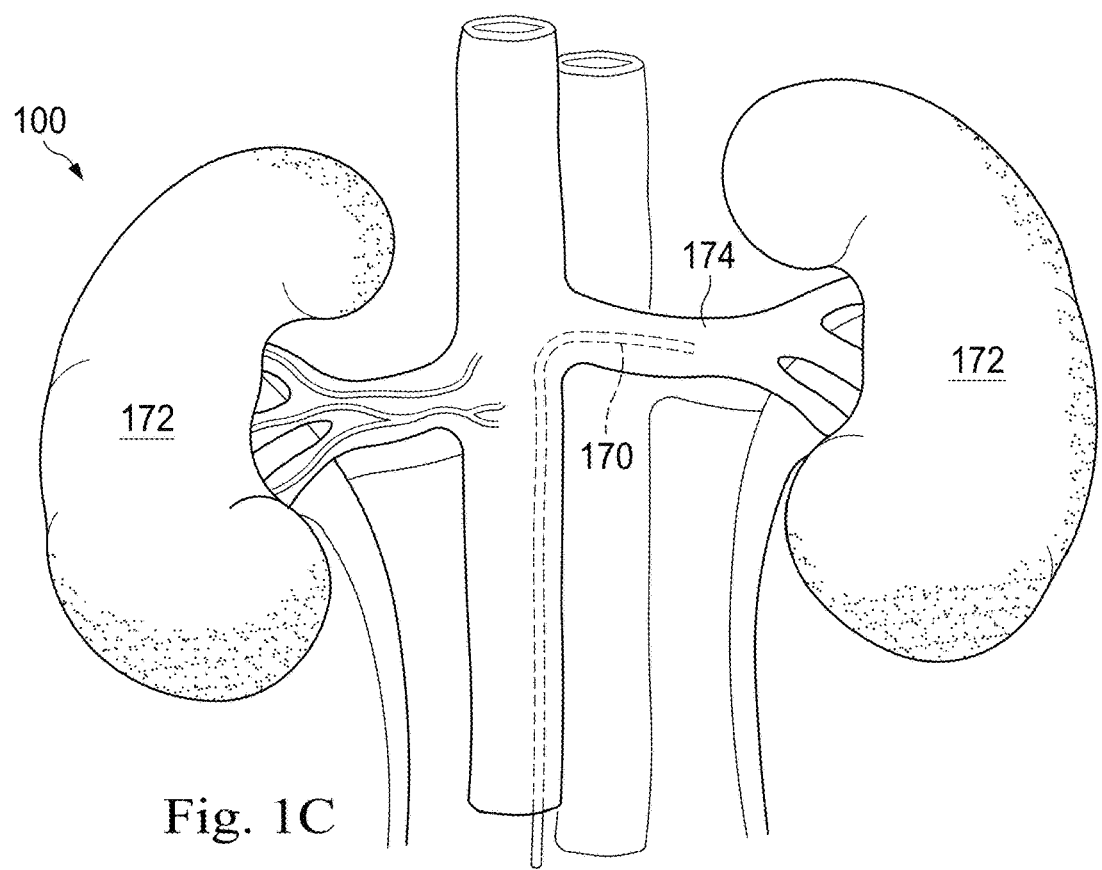

FIGS. 1A, 1B, and 1C are schematic drawings depicting a medical system including an invasive intravascular system in various applications according to some embodiments of the present disclosure. In general, the medical system 100 may be a single modality medical system or a multi-modality medical system. In that regard, a multi-modality medical system provides for coherent integration and consolidation of multiple forms of acquisition and processing elements designed to be sensitive to a variety of methods used to acquire and interpret human biological physiology and morphological information and/or coordinate treatment of various conditions.

With reference to FIG. 1A, the imaging system 101 is an integrated device for the acquisition, control, interpretation, and display of one or more modalities of medical sensing data. Accordingly, in some embodiments, the imaging system 101 is a single modality imaging system, such as an IVUS imaging system, whereas, in some embodiments, the imaging system 101 is a multi-modality imaging system. In one embodiment, the imaging system 101 includes a computer system with the hardware and software to acquire, process, and display medical imaging data, but, in other embodiments, the imaging system 101 includes any other type of computing system operable to process medical data. In the embodiments in which the imaging system 101 includes a computer workstation, the system includes a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and/or a network communication device such as an Ethernet controller and/or wireless communication controller. In that regard, in some particular instances, the imaging system 101 is programmed to execute steps associated with the data acquisition and analysis described herein. Accordingly, it is understood that any steps related to data acquisition, data processing, instrument control, and/or other processing or control aspects of the present disclosure may be implemented by the imaging system 101 using corresponding instructions stored on or in a non-transitory computer readable medium accessible by the processing system. In some instances, the imaging system 101 is portable (e.g., handheld, on a rolling cart, etc.). Further, it is understood that in some instances imaging system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the imaging system 101 being located in the control room. In other embodiments, the imaging system 101 may be located elsewhere, such as in the catheter lab 102, in a centralized area in a medical facility, or at an off-site location accessible over a network. For example, the imaging system 101 may be a cloud-based resource. The catheter lab 102 includes a sterile field generally encompassing a procedure area, whereas the associated control room 104 may or may not be sterile depending on the requirements of a procedure and/or health care facility. The catheter lab and control room may be used to perform on a patient any number of medical sensing procedures such as angiography, intravascular ultrasound (IVUS), photoacoustic IVUS, forward looking IVUS (FL-IVUS), virtual histology (VH), intravascular photoacoustic (IVPA) imaging, pressure determination, optical pressure determination, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or multiple procedures. In any case, the catheter lab 102 includes a plurality of medical instruments including medical sensing devices that collect medical sensing data in various different medical sensing modalities from the patient 106.

In the illustrated embodiment of FIG. 1A, instruments 108 and 110 are medical sensing devices that may be utilized by a clinician to acquire medical sensing data about the patient 106. In a particular instance, the device 108 collects medical sensing data in one modality, and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. In some embodiments, device 108 and 110 collect medical sensing data in different versions of similar modalities. For example, in one such embodiment, device 108 collects pressure data, and device 110 collects FFR (a pressure-based measurement) data. In another such embodiment, device 108 collects 20 MHz IVUS data, and device 110 collects 40 MHz IVUS data. Accordingly, the devices 108 and 110 may be any form of device, instrument, or probe sized and shaped to be positioned within a vessel, attached to an exterior of the patient, or scanned across a patient at a distance.

In the illustrated embodiment of FIG. 1A, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114, respectively, couple the IVUS catheter 108 and OCT catheter 110 to the imaging system 101. In particular, the IVUS PIM 112 and the OCT PIM 114 are operable to receive medical sensing data collected from the patient 106 by the IVUS catheter 108 and OCT catheter 110, respectively, and are operable to transmit the received data to the imaging system 101 in the control room 104. In one embodiment, the PIMs 112 and 114 include analog to digital (A/D) converters and transmit digital data to the imaging system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the imaging system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the imaging system 101. In some embodiments, the imaging system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the imaging system 101. In one embodiment, the angiogram system 117 is communicatively coupled to the processing system of the imaging system 101 through an adapter device. Such an adaptor device may transform data from a proprietary third-party format into a format usable by the imaging system 101. In some embodiments, the imaging system 101 is operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the imaging system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 9, in some embodiments, the bedside controller 118 includes a user interface (UI) framework service through which workflows associated with multiple modalities may execute. Thus, the bedside controller 118 may be capable displaying workflows and diagnostic images for multiple modalities allowing a clinician to control the acquisition of multi-modality medical sensing data with a single interface device.

A main controller 120 in the control room 104 is also communicatively coupled to the imaging system 101 and, as shown in FIG. 1A, is adjacent to catheter lab 102. In the current embodiment, the main controller 120 is similar to the bedside controller 118 in that it includes a touch screen and is operable to display a multitude of GUI-based workflows corresponding to different medical sensing modalities via a UI framework service executing thereon. In some embodiments, the main controller 120 is used to simultaneously carry out a different aspect of a procedure's workflow than the bedside controller 118. In alternative embodiments, the main controller 120 includes a non-interactive display and standalone controls such as a mouse and keyboard.

The medical system 100 further includes a boom display 122 communicatively coupled to the imaging system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality imaging system 101 is communicatively coupled to a data network 125. In the illustrated embodiment, the data network 125 is a TCP/IP-based local area network (LAN); however, in other embodiments, it may utilize a different protocol such as Synchronous Optical Networking (SONET), or may be a wide area network (WAN). The imaging system 101 may connect to various resources via the network 125. For example, the imaging system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality imaging system 101 via the network 125 to allow a doctor or other health professional to access the aspects of the medical system 100 remotely. For instance, a user of the network console 130 may access patient medical data such as diagnostic images collected by multi-modality imaging system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the imaging system 101 via a wired connection such as a standard copper link or a fiber optic link, but, in alternative embodiments, the tools may be connected to the imaging system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the imaging system 101 so as to contribute additional and/or different functionality to the medical system 100.

With reference now to FIG. 1B, an application of the medical system 100 includes a coronary catheterization procedure. In a coronary catheterization procedure, a medical sensing instrument including a sensing catheter 150 is passed into a blood vessel of the heart 152 via the aorta 154. In some embodiments, a guide wire 156 is first advanced into the heart 152 through a large peripheral artery leading into the aorta 154. Once the guide wire 156 is properly located, a guide catheter 158 is advanced over the guide wire. The sensing catheter 150 is then directed into place by traveling over the guide wire 156 and inside the guide catheter 158. In the illustrated embodiment, the distal tip of the sensing catheter 150 is advanced until it is positioned in the left coronary artery 160. The sensing catheter 150 is activated, and signals are passed between the catheter 150 and components of the system 100 such as the PIM 112 and/or the imaging system 101 of FIG. 1A. In the example of an IVUS sensing catheter 150, signals sent from the IVUS PIM 112 to one or more ultrasound transducers cause the transducers to emit a specified ultrasonic waveform. Portions of the ultrasonic waveform are reflected by the surrounding vasculature and received by a one or more receiving transducers of the catheter 150. The resulting echo signals are amplified for transmission to the IVUS PIM 112. In some instances, the PIM 112 amplifies the echo data, performs preliminary pre-processing of the echo data, and/or retransmits the echo data to the imaging system 101. The imaging system 101 aggregates and assembles the received echo data to create an image of the vasculature for display.

In some exemplary applications, the IVUS sensing catheter 150 is advanced beyond the area of the vascular structure to be imaged and pulled back as the transducers are operating, thereby exposing and imaging a longitudinal portion of the vessel. To ensure a constant velocity, a pullback mechanism is used in some applications. A typical withdraw velocity is 0.5 mm/s, although other rates are possible based on beam geometry, sample speed, and the processing power of the system. In some embodiments, the catheter 150 includes an inflatable balloon portion. As part of a treatment procedure, the device may be positioned adjacent to a stenosis (narrow segment) or an obstructing plaque within the vascular structure and inflated in an attempt to widen the restricted area.

With reference now to FIG. 1C, another application of the medical system 100 includes a renal catheterization procedure. In a renal catheterization procedure, the sensing catheter 170 is passed into a blood vessel of the kidneys 172 via the aorta. This may involve first advancing a guide wire and/or guide catheter and using the guide device(s) to control the advance of the sensing catheter 170. In the illustrated embodiment, the distal tip of the sensing catheter 170 is advanced until it is located in the right renal artery 174. Then, the sensing catheter 170 is activated and signals are passed between the catheter 170 and components of the system 100 such as the PIM 112 and/or the imaging system 101 of FIG. 1A. In the example of an IVUS sensing catheter 170, the signals contain echo data transmitted from the catheter 170 to the imaging system 101 by way of the IVUS PIM 112. The structures of the renal vasculature differ from those of the cardiac vasculature. Vessel diameters, tissue types, and other differences may mean that operating parameters suited to cardiac catheterization are less well suited to renal catheterization and vice versa. Furthermore, renal catheterization may target different structures, seeking to image the renal adventitia rather than arterial plaques, for example. For these reasons and more, the imaging system 101 may support different operating parameters for different applications such as cardiac and renal imaging. Likewise, the concept may be applied to any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body.

Figure 2:
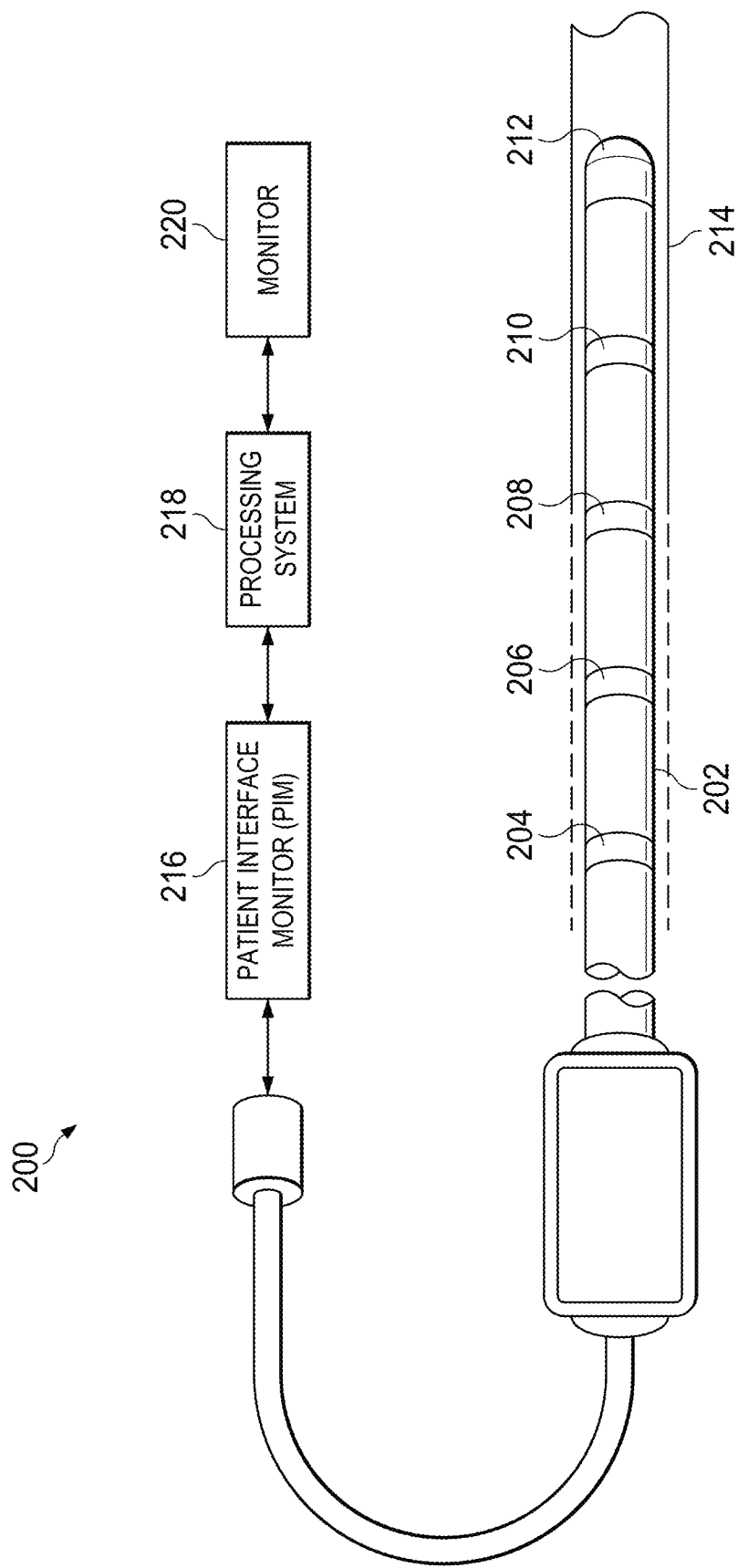
FIG. 2 is a diagrammatic schematic view of a medical sensing system according to some embodiments of the present disclosure.

FIG. 2 is a diagrammatic schematic view of a medical sensing system 200 according to some embodiments of the present disclosure. The medical sensing system 200 is suitable for use as a standalone system or as part of a larger medical imaging system including the medical system 100 of FIGS. 1A, 1B, and 1C. In that regard, elements of the sensing system 200 may be incorporated into elements of medical system 100. In alternate embodiments, elements of the sensing system 200 are distinct from and are in communication with elements of the medical system 100.

The medical sensing system 200 includes an elongate member 202. As used herein, "elongate member" or "flexible elongate member" includes at least any thin, long, flexible structure that can be inserted into the vasculature of a patient. While the illustrated embodiments of the "elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

Elongate member 202 includes sensors (e.g., sensors 204, 206, 208, and 210) disposed along the length of the member 202. In some embodiments, the elongate member 202 includes one or more sensors (e.g., sensor 212) disposed at the distal end. In various embodiments, sensors 204, 206, 208, 210, and 212 correspond to sensing modalities such as flow, optical flow, IVUS, photoacoustic IVUS, FL-IVUS, pressure, optical pressure, fractional flow reserve (FFR) determination, coronary flow reserve (CFR) determination, OCT, transesophageal echocardiography, image-guided therapy, other suitable modalities, and/or combinations thereof. In an exemplary embodiment, sensors 204 and 208 are IVUS ultrasound transceivers, sensors 206 and 210 are fluid flow sensors, and sensor 212 is a pressure sensor. In another embodiment, sensors 204, 206, 208, and 210 are pressure sensors and sensor 212 is an FL-IVUS transceiver. Other embodiments incorporate other combinations of sensors, and no particular sensor or combination of sensors is required for any particular embodiment.

The electronic, optical, and/or electro-optical sensors, components, and associated communication lines are sized and shaped to allow for the diameter of the flexible elongate member 202 to be very small. For example, the outside diameter of the elongate member 202, such as a guide wire or catheter, containing one or more electronic, optical, and/or electro-optical components as described herein is between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members 202 incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

The distal end of the elongate member 202 is advanced through a vessel 214. Vessel 214 represents fluid filled or surrounded structures, both natural and man-made, within a living body and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to natural structures, elongate member 202 may be used to examine man-made structures such as, but without limitation, heart valves, stents, shunts, filters and other devices positioned within the body, for example, a guide wire or guide catheter.

When the sensors are active, a communications channel, such as an optical fiber, a conductor bundle, and/or a wireless transceiver, present in the elongate member 202 carries sensor data to a patient interface monitor (PIM) 216 coupled to the proximal end of the elongate member 202. The PIM 216 may be substantially similar to the IVUS PIM 112 and/or OCT PIM 114 disclosed with reference to FIG. 1A. For example, the PIM 216 is operable to receive medical sensing data collected using the sensors and is operable to transmit the received data to a processing system 218. In some embodiments, the PIM 216 performs preliminary processing of the sensing data prior to transmitting the data to the processing system 218. In examples of such embodiments, the PIM 216 performs amplification, filtering, time-stamping, identification, and/or aggregating of the data. The PIM 216 also transfers data such as commands from the processing system 218 to the sensors of the elongate member 202. In an exemplary embodiment, these commands include commands to enable and disable sensors and/or to configure modes of operation for individual sensors. In some embodiments, the PIM 216 also supplies power to drive the operation of the sensors.

The PIM 216 is communicatively coupled to the processing system 218, which governs sensor operation and data acquisition, processing, interpretation, and display. In many respects, the processing system 218 is substantially similar to the imaging system 101 of FIG. 1A. In that regard, the processing system 218 receives sensor data from the sensors of the elongate member 202 via the PIM 216, processes the sensor data to render it suitable for display, and presents the processed sensor data at a user display 220.

In many embodiments, the medical sensing system 200 leverages the ability of the processing system 218 to support an increased number of sensors. In some such embodiments, this allows operators to locate vascular abnormalities or other structures that are not visible using external imaging. In one such embodiment, a series of measurements is taken along the length of the elongate member 202 in order to detect the structure of interest without necessarily relocating the elongate member 202. This may take the form of a virtual pullback. Once the structure of interest is located, detailed measurements may be taken of the surrounding area. In this way, the system 200 provides detailed analysis of the surrounding vasculature without a physical pullback and/or without exchanging devices.

FIG. 3 is a diagrammatic schematic view of a portion of an electromechanical medical sensing system 300 according to some embodiments of the present disclosure. The system 300 may be substantially similar to the sensing system 200 disclosed with reference to FIG. 2. In that regard, the system 300 incorporates multiple sensors (e.g., sensors 304, 306, and 308) in the distal end of an elongate member 302 of the sensing system 300. While, in the interest of clarity, only three sensors are illustrated, further embodiments incorporate any number of sensors including embodiments with 4, 8, 16, 32, and more sensors. The sensors 304, 306, and 308 correspond to one or more sensing modalities such as flow, optical flow, IVUS, photoacoustic IVUS, FL-IVUS, pressure, optical pressure, FFR determination, CFR determination, OCT, transesophageal echocardiography, image-guided therapy, and/or other suitable modalities. For example, in some embodiments, sensors 304, 306, and 308 include IVUS transducers. In that regard, the sensors may include piezoelectric micromachine ultrasound transducers (PMUTs), capacitive micromachined ultrasound transducers (CMUT), piezoelectric transducers (PZTs), and/or combination thereof. U.S. Pat. No. 6,238,347, entitled "ULTRASONIC TRANSDUCER ARRAY AND METHOD OF MANUFACTURING THE SAME," U.S. Pat. No. 6,641,540, entitled "MINIATURE ULTRASOUND TRANSDUCER," U.S. Pat. No. 7,226,417, entitled "HIGH RESOLUTION INTRAVASCULAR ULTRASOUND TRANSDUCER ASSEMBLY HAVING A FLEXIBLE SUBSTRATE," and U.S. Pat. No. 7,914,458, entitled "CAPACITIVE MICROFABRICATED ULTRASOUND TRANSDUCER-BASED INTRAVASCULAR ULTRASOUND PROBES," disclose IVUS transducers in more detail and are herein incorporated by reference. Examples of commercially available products that include suitable IVUS transducers include, without limitation, the Eagle Eye® series of IVUS catheters, the Revolution® IVUS catheter, and the Visions® series of IVUS catheters, each available from Volcano Corporation. For the purposes of this disclosure, such transducers are referred to as "electromechanical transducers" due to the electrical interface and electromechanical operation. This is in contrast to the optical interface and photoacoustic operation of photoacoustic transducers disclosed in detail below.

As another example, in some embodiments, sensors 304, 306, and 308 include pressure sensors and may take the form of a piezo-resistive pressure sensor, a piezoelectric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure sensor are implemented as a solid-state component manufactured using semiconductor and/or other suitable manufacturing techniques. Examples of commercially available guide wire products that include suitable pressure sensors include, without limitation, the PrimeWire PRESTIGE® pressure guide wire, the PrimeWire® pressure guide wire, and the ComboWire® XT pressure and flow guide wire, each available from Volcano Corporation.

The sensors 304, 306, and 308 are distributed along the distal end of the elongate member 302 and are connected to a transmission line bundle 310 that terminates in a PIM coupler (not illustrated) at a proximal end of the system 300. The transmission line bundle 310 provides an electrical interface between a PIM and sensors 304, 306, and 308, and contains any number of conductors, including embodiments with 2, 3, 4, 6, 7, and 8 total conductors, in any arrangement. As the sensors 304, 308, and 308 are coupled to an electrical interface (e.g., transmission line bundle 310) and are electrically operated, they are referred to as "electromechanical sensors" for the purposes of this disclosure.

In contrast to the electrical interface of system 300, FIG. 4 is a diagrammatic schematic view of a portion of an optical sensing system 400 having an optical interface according to some embodiments of the present disclosure. The system 400 may be substantially similar to the sensing system 200 disclosed with reference to FIG. 2. In that regard, the system 400 incorporates multiple optical sensors (e.g., sensors 404, 406, and 408) in the distal end of an elongate member 402 of the sensing system 400. While, in the interest of clarity, only three sensors are illustrated, further embodiments incorporate any number of sensors including embodiments with 4, 8, 16, 32, and more sensors. The sensors 404, 406, and 408 correspond to sensing modalities such as flow, optical flow, IVUS, photoacoustic IVUS, FL-IVUS, pressure, optical pressure, FFR determination, CFR determination, OCT, transesophageal echocardiography, image-guided therapy, and/or other suitable modalities. As an example, in some embodiments, sensors 404, 406, and 408 include photoacoustic IVUS transducers. U.S. Pat. No. 7,245,789, entitled "SYSTEMS AND METHODS FOR MINIMALLY-INVASIVE PHOTOACOUSTIC IMAGING," U.S. Pat. No. 6,659,957, entitled "PHOTOACOUSTIC IMAGING DEVICE," and U.S. patent application Ser. No. 12/571,724, entitled "OPTICAL ULTRASOUND RECEIVER, disclose photoacoustic IVUS devices in detail and are herein incorporated in their entirety. Furthermore, additional suitable photoacoustic IVUS transducers are disclosed below with reference to FIGS. 6-9.

As a further example, in some embodiments, sensors 404, 406, and 408 include optical pressure sensors. U.S. Pat. No. 7,689,071, entitled "FIBER OPTIC PRESSURE SENSOR FOR CATHETER USE," U.S. Pat. No. 8,151,648, entitled "ULTRA-MINIATURE FIBER-OPTIC PRESSURE SENSOR SYSTEM AND METHOD OF FABRICATION," and U.S. application Ser. No. 13/415,514, entitled "MINIATURE HIGH SENSITIVITY PRESSURE SENSOR," disclose optical pressure sensors in detail and are herein incorporated in their entirety.

Sensors 404, 406, and 408 are connected to a fiber core 410 that optically couples the sensors to a PIM (not shown). In some embodiments, the optical fiber core 410 is configured for spatial multiplexing of sensor data. Spatial multiplexing divides a common conduit such as a fiber core 410 into physical regions, where each physical region of the conduit is reserved for a particular device. In one such embodiment, the fiber core 410 comprises multiple strands of optical fibers, and each strand or strand group is exclusively coupled to a single sensor. Spatial multiplexing allows the PIM to address individual sensors by transmitting and receiving data using the corresponding strand or strand group.

In some embodiments, sensor data is wavelength division multiplexed. Wavelength division optical multiplexing assigns each data channel a unique portion of the spectrum. Sufficient spacing is allocated between channels to reduce crosstalk and to allow for manufacturing variability. The data channels can then be transmitted concurrently over a common conduit, such as fiber core 410, without interference. In such embodiments, optical filters or gratings are located along the length of the fiber core 410 and are tuned to demultiplex the appropriate signals and direct them towards the corresponding sensor. Wavelength division multiplexing may be particularly useful for embodiments where the optical fiber core 410 is rotated independently of the PIM, such as rotational IVUS and rotational OCT, as the transmission of data does not rely on an alignment of fiber core strands relative to the PIM. As a further example, in some embodiments, the sensor data is time-division multiplexed, although no particular multiplexing scheme is required for any particular embodiment.

FIGS. 5A and 5B are diagrammatic schematic views of a medical sensing device used in a catheterization procedure 500 according to some embodiments of the present disclosure. With reference first to FIG. 5A, an elongate member 502 of the medical sensing device is advanced into a vessel 504. The elongate member 502 is substantially similar to those disclosed with reference of FIGS. 2-4. In that regard, the elongate member incorporates sensors 506 (including sensors 506a-d) in the distal end of the elongate member 502. The sensors 506 correspond to one or more sensing modalities such as flow, optical flow, IVUS, photoacoustic IVUS, FL-IVUS, pressure, optical pressure, FFR determination, CFR determination, OCT, transesophageal echocardiography, image-guided therapy, and/or other suitable modalities. Vessel 504 represents fluid filled or surrounded structures, both natural and man-made, within a living body and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to natural structures, elongate member 502 may be used to examine man-made structures such as, but without limitation, heart valves, stents, shunts, filters and other devices positioned within the body, for example, a guide wire or guide catheter.

Many cardiovascular structures of interest cannot be accurately located using external means. In many other applications, while the location of the both structure of interest and the elongate member 502 can be determined generally, achieving the proper alignment of the two proves challenging. Therefore, it may be advantageous to use the array of sensors 506 arranged along the longitudinal length of the elongate member 502 to determine the location of the structure of interest. In the illustrated embodiment, the elongate member 502 is advanced into the vessel 504 until it is in the general area of structures 508, 510, and 512. In various applications, structures of interest include bifurcations, stenoses, plaques, vascular dissections, lesions, stents, and/or other suitable venous morphology. Once in position, a series of measurements are obtained from which the vascular structure can be detected.

For example, in some embodiments, sensors 506 include pressure sensors, and a series of fractional flow reserve ratios are calculated. FFR is a currently accepted technique for assessing the severity of a stenosis in a blood vessel, including ischemia-causing lesions, and may be used to determine other types of vascular structures. FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Further measurements such as Instant Wave-Free Ratio™ Functionality data (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," which discloses the use of pressure ratios that are available without a hyperemic agent, are also suitable for use in some embodiments. From the iFR® and/or FFR data, structures such as stenoses can be inferred. For example, in some embodiments, an FFR below a threshold (e.g., 0.80) suggests that a structure such as a stenosis lies between the proximal and distal sensors 506. Thus, the location of the stenosis can be inferred from the known location of the sensors 506 on either side of where the FFR measurement drops below the threshold.

In other exemplary embodiments, sensors 506 such as IVUS transducers or OCT transceivers are used to take cross-sectional or forward-looking views of the vessel 504 along the length of the elongate member 502. In such embodiments, the location of vascular structures (e.g., structures 508, 510, and 512) may be determined by examining differences in images across sensors, by a tissue characterization process such as the process disclosed in detail below, and/or by other diagnostic examination of the data.

In further exemplary embodiments, other combinations of sensors 506 and modalities are used to locate vascular structures, and one of skill in the art will recognize that the location of a structure can be determined using a variety of sensors 506 and modalities without departing from the spirit of the present disclosure.

In addition to locating structures, the data collected by the sensors 506 can be utilized for diagnostic purposes. For example, in one embodiment, the sensors 506 include pressure sensors, and a series of FFR determinations are taken along the length of the member 502. In the example, the data indicates multiple plaque stenoses (e.g., structures 510 and 512). Therefore, an FFR ratio is calculated to determine the combined effect using a proximal sensor proximal to all of the plaques and a distal sensor distal to all of the plaques (e.g., sensor 506a and 506d). Additional FFR ratios are also calculated to determine the individual effect of each plaque. These individual FFR ratios are calculated using sensors located proximal and distal to each plaque such that the sensors are approximately between each plaque and the next (e.g., sensors 506a and 506b for structure 510 and sensors 506c and 506d for structure 512). In this way, the operator can distinguish stenoses that are individually benign but collectively acute, and can determine which obstructions have the largest overall contribution.

Further embodiments utilize other multi-site determinations to evaluate overall vascular health. For example, in one such embodiment, the elongate member 502 is used to perform a virtual pullback. In response to a user command, the data collected using the sensors 506 may be presented to the user in sequence. Stepping through the sensors in order of location simulates a pullback of a single sensor through the vessel 504 without actually withdrawing the elongate member 502. This allows subsequent measurements of the simulated pullback to be performed without repositioning the device.

Referring now to FIG. 5B, the elongate member 502, the incorporated sensors 506, and the vessel 504 are substantially similar to those disclosed with reference to FIG. 5A. However, the elongate member also includes a detailed sensing region 514. Once a structure of interest is located, the detailed sensing region 514 may be used to examine the structure. The detailed sensing region 514 is maneuvered into position adjacent to the structure (e.g., structure 512), and data is collected using the associated sensors 506. In the illustrated embodiment, the detailed sensing region 514 has tighter sensor spacing than the remainder of the elongate member 502. In addition or in the alternative, the detailed sensing region 514 may incorporate different types of sensors that correspond to different modalities or sets of modalities. In some embodiments, the sensors of the detailed sensing region have a higher sensing resolution along the axial length of the elongate member 502 than other sensors of the elongate member 502. In various further embodiments, the detailed sensing region 514 has other sensing differences as compared to the remainder of the elongate member 502. The detailed sensing region 514 allows for in depth sensing and analysis when desired, but reduces device complexity, cost, and/or system requirements by limiting the number of sensors 506 allocated for detailed analysis.

Figure 6:
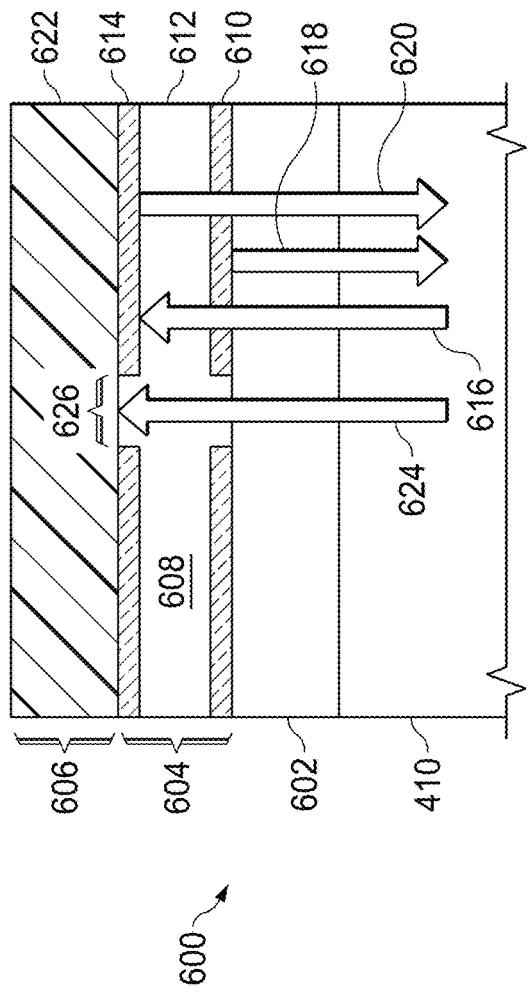
FIG. 6 is a diagrammatic schematic view of a photoacoustic IVUS transducer according to some embodiments of the present disclosure.

FIG. 6 is a diagrammatic schematic view of a photoacoustic IVUS transducer 600 according to some embodiments of the present disclosure. The illustrated transducer 600 is suitable for use in a sensing device such as instruments 108 and 110 of FIG. 1A, elongate member 202 of FIG. 2, and/or elongate member 402 of FIG. 4. Furthermore, because the transducer 600 includes an ultrasound membrane and a reflective etalon structure arranged in a vertical stack, the device is particularly well suited for use in an end-looking photoacoustic IVUS sensing device.

The transducer 600 is physically coupled to a fiber core 410 that acts as a conduit for transmitting optical signals along a longitudinal length of a sensing device such as a catheter, guide catheter or guide wire. The fiber core 410 communicatively couples the transducer 600 at a distal portion of the device to a PIM at a proximal portion. The transducer 600 itself includes a receiver portion 604 and a transmitter portion 606 coupled to the fiber core 410 via a transparent substrate 602, which offers structural support of the transducer 600 during manufacturing, assembly, and/or operation. The receiver portion 604 includes an etalon 608, a form of sensor that can be optically probed to determine the strength of ultrasound echoes acting on the etalon 608. The etalon 608 includes two partially reflective mirrors (e.g., initial mirror 610 and terminal mirror 614) separated by a spacer layer 612. In an exemplary embodiment, the distance between the initial mirror 610 and the terminal mirror 614 and likewise the thickness of the spacer layer 612 is approximately 5.9 μm. In an exemplary embodiment, the thickness of each of the initial mirror 610 and the terminal mirror 614 is approximately 30 nm. In some embodiments, both mirrors 610 and 614 have substantially equivalent reflectivity. In some further embodiments, the terminal mirror 614 has substantially higher reflectivity than the initial mirror 610.

When a light source, such as a probing laser, is directed at the etalon 608 as illustrated by arrow 616, a portion of the light energy is reflected by the initial mirror 610 as illustrated by arrow 618. This defines the first of two optical paths. A second portion of the light energy passes through initial mirror 610 and the spacer layer 612 and is reflected by the terminal mirror 610 as illustrated by arrow 620. This defines the second optical path. Differences in the optical paths affect the phase of the two reflected signals relative to one another. These differences may be measured by examining the interference pattern of the reflected signals.

In an embodiment, both reflected signals are carried by the fiber core 410 to the PIM (not illustrated) where the interference pattern is analyzed. A baseline interference pattern is established representing a state where negligible ultrasonic pressure is acting on the etalon 608. As compressive and expansive forces, such as those caused by reflected ultrasound echoes, are directed upon the etalon 608, the forces alter the optical path and, thus, the interference pattern. In some embodiments, the material of the spacer layer 612 exhibits a change in physical dimension under stress. In some embodiments, the material of the spacer layer 612 exhibits a change in refractive index under stress. Thus, changes in the optical path can be a function of the distance between the initial mirror 610 and terminal mirror 610 and/or a function of the refractive index of the spacer layer 612. Put another way, a change in the refractive index of the spacer layer 612 can induce a change in optical path length, even though the physical distance between mirror 610 and mirror 614 has not substantially changed. The aforementioned changes in the optical paths produce changes in the interference pattern, and, by comparing subsequent interference patterns to the baseline, the PIM obtains corresponding force measurements.

The transducer 600 also includes an emitter portion 606 disposed above the receiver portion 604. The emitter portion includes an expansive film 622 that, in various embodiments, is made of an elastic biocompatible material such as one or more of polydimethylsiloxane (PDMS), polyvinylidene fluoride (PVDF), and/or other suitable materials. In one embodiment, a PDMS film 622 is formed to a thickness of approximately 11 μm. The film 622 expands when heated with optical energy such as laser energy. Rapid expansion and contraction caused by, for example, a pulsed laser illustrated by arrow 624 causes the film 622 to generate an ultrasonic waveform. In an exemplary embodiment, the pulsed laser produces a 25 nanosecond pulse with a 50 nanosecond rest to allow the film 622 to cool and induces a 20 MHz ultrasound pulse. In some embodiments, the mirrors 610 and 614 of the etalon 608 are adapted to transmit energy from the pulsed laser through the mirrors to reach the film 622 while reflecting energy from the probing laser. In some embodiments, the mirrors 610 and 614 have an aperture 626 formed therein to allow transmission of the pulsed laser through the etalon 608. An exemplary aperture 626 is approximately 2 mm wide.

Figure 7A:
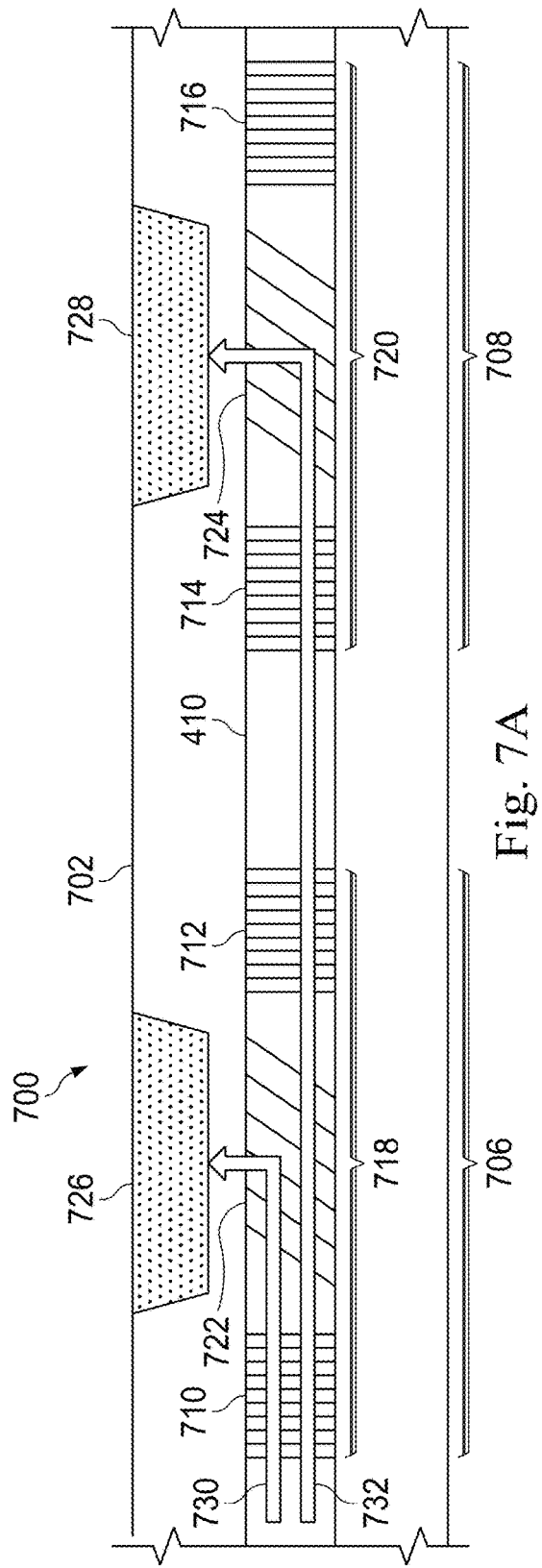
FIG. 7A is a diagrammatic schematic view of a portion of a photoacoustic IVUS system in a transmit mode according to some embodiments of the present disclosure.

FIG. 7A is a diagrammatic schematic view of a portion of a photoacoustic IVUS system 700 according to some embodiments of the present disclosure. The illustrated system 700 is suitable for use in a sensing device such as instruments 108 and 110 of FIG. 1A and may be substantially similar to system 200 of FIG. 2 and/or system 400 of FIG. 4. In that regard, the photoacoustic IVUS system 700 has an elongate member 702 that includes an optical fiber core 410. The elongate member also includes two side-looking photoacoustic ultrasound transducers 706 and 708 disposed around the fiber core 410. Further embodiments incorporate other numbers of transducers and may incorporate both photoacoustic and electromechanical transducers.

The photoacoustic ultrasound transducers 706 and 708 each include a pair of perpendicularly aligned fiber Bragg gratings (e.g., gratings 710 and 712 of transducer 706 and gratings 714 and 716 of transducer 708) that form etalons 718 and 720. Each transducer also includes a blazed (angled) fiber Bragg grating (e.g., gratings 722 and 724) that direct light energy towards a diaphragm (e.g., diaphragms 726 and 728) of expansive film such as one or more of polydimethylsiloxane (PDMS), polyvinylidene fluoride (PVDF), and/or other suitable materials. The fiber Bragg gratings 710, 712, 714, 716, 722, and 724 are configured to reflect and transmit particular wavelengths of light. A uniform pitch fiber Bragg grating reflects light within a narrowband frequency range centered about a Bragg wavelength λ given by $\lambda = 2\Lambda$, where n is the index of the fiber core 410 and $\Lambda$ is the grating period. Thus, by tuning the pitch of the fiber Bragg grating, the optical response of the grating can be tuned. In particular, the pitch of the fiber Bragg gratings may be tuned to demultiplex signals transmitted along the fiber core 410 in a wavelength division multiplexing communication scheme, as will be disclosed in more detail below. In brief, tuned fiber Bragg gratings allow the independent control of each transducer (e.g., transducers 706 and 708) over a multiplexed optical channel.

FIG. 7A illustrates this independent control of transducers 706 and 708 in a transmit mode. The first blazed fiber Bragg grating 722 reflects laser energy of a first wavelength. Because of the angle of the Bragg grating, the reflected energy is directed towards the diaphragm 726 as illustrated by arrow 730 where it heats the film of diaphragm 726 and causes an ultrasonic impulse. In contrast, the first blazed fiber Bragg grating 722 transmits, rather than reflects, laser energy of a second wavelength. Accordingly, independent of the operation of the first transducer 706, energy of the second wavelength is conducted along the fiber core 410 as illustrated by arrow 732 until it reaches the second blazed fiber Bragg grating 724. The pitch of the second grating 724 is configured to reflect laser energy of the second wavelength towards the film of the diaphragm 728 where it heats the diaphragm 728 and causes an ultrasonic impulse. This concept is not limited to two transducers, and in various exemplary embodiments 4, 8, 16, 32, and more transducers are arranged on a common fiber core.

FIG. 7B is a diagrammatic schematic view of a portion of a photoacoustic IVUS system 750 according to some embodiments of the present disclosure. The illustrated system 750 is suitable for use in a sensing device such as instruments 108 and 110 of FIG. 1A and may be substantially similar to system 200 of FIG. 2 and/or system 400 of FIG. 4. The photoacoustic IVUS system 750 is substantially similar to system 700 disclosed with respect to FIG. 7A. In that regard, the system 750 includes an elongate member 702, a fiber optic core 410, and a photoacoustic transducer 706 comprising perpendicular fiber Bragg gratings 710 and 712, a blazed (angled) fiber Bragg grating 722, and a diaphragm 726 substantially similar to those described with respect to FIG. 7A.

FIG. 7B illustrates the operation of the transducer 706 in receive mode. The perpendicular fiber Bragg gratings 710 and 712 form an etalon 718, which may be used to measure ultrasonic echo signals received by the transducer 706. When a light source, such as a probing laser, is directed at the etalon 718 as illustrated by arrow 752, a portion of the light energy is reflected by the first fiber Bragg grating 710 as illustrated by arrow 754. A second portion of the light energy passes through the segment of the fiber core 410 between the first and second perpendicular fiber Bragg gratings 710 and 712. The blazed fiber Bragg grating 722 does not hinder the passage of this light energy as it is configured to transmit light energy having the probing wavelength. This may be achieved by configuring the pitch of the blazed fiber Bragg grating 722 as disclosed above. Accordingly, the second portion of the light energy continues through the fiber core 410 until it is reflected by the second perpendicular grating 712 as indicated by arrow 756.

Differences in the optical paths affect the phase of the two reflected signals relative to one another. These differences may be measured by examining the interference pattern of the reflected signals. In an embodiment, both reflected signals are carried by the fiber core 410 to the PIM (not illustrated) where the interference pattern is analyzed. A baseline interference pattern is established representing a state where negligible ultrasonic pressure is acting on the etalon 718. As compressive and expansive forces, such as those caused by reflected ultrasound echoes, are directed upon the etalon 718, the forces alter the optical path and, thus, the interference pattern. By comparing subsequent interference patterns to the baseline, corresponding force measurements can be obtained. Differences in the optical paths can be a function of the distance between the first perpendicular grating 710 and the second perpendicular grating 712 as well as a function of the refractive index of the fiber core 410 between the gratings 710 and 712. Thus, a change in the refractive index of the fiber core 410 can induce a change in optical path length, even though the physical distance between the gratings 710 and 712 has not substantially changed.

In some embodiments, multiple transducer etalons 718 are arranged along a fiber core 410. In accordance with the principles disclosed above, the gratings of each etalon 718 are configured to reflect a wavelength unique to the transducer and to transmit wavelengths characteristic of the other transducers. This allows the independent measurement of ultrasonic echo data at any particular transducer by probing the transducer with the characteristic wavelength and measuring the resulting interference pattern. In various exemplary embodiments, 2, 4, 8, 16, 32, and more transducer etalons are arranged on a common fiber core, each transducer being independently addressable via a unique optical wavelength.

FIG. 8 is a diagrammatic schematic view of a portion of a multi-modality optical system according to some embodiments of the present disclosure. The illustrated system 800 is suitable for use in a sensing device such as instruments 108 and 110 of FIG. 1A and may be substantially similar to system 200 of FIG. 2 and/or system 400 of FIG. 4. Furthermore, the system 800 is substantially similar to the systems 700 and 750 disclosed with reference to FIGS. 7A and 7B. In that regard, the system 800 includes photoacoustic transducers 706 and 708, which in turn include perpendicular fiber Bragg gratings that form etalons and blazed fiber Bragg gratings that direct light energy from a fiber core 410 towards elastic diaphragms.

The system 800 also includes one or more additional sensors arranged along the system 800. These sensors may be located along the longitudinal length of the system 800 such as sensor 802 and/or at the tip of the system 800 such as sensor 804. In various embodiments, sensors 802 and 804 include ultrasound transducers, OCT sensors, pressure sensors, flow sensors, and/or other suitable medical sensors and are electrically and/or optically operated. In an exemplary embodiment, sensor 802 includes an optical pressure sensor. In another exemplary embodiment, sensor 804 includes an optical FL-IVUS transducer. Thus, the system 800 incorporates a diverse array of sensors corresponding to a wide assortment of modalities into a single sensing instrument.

Figure 9:
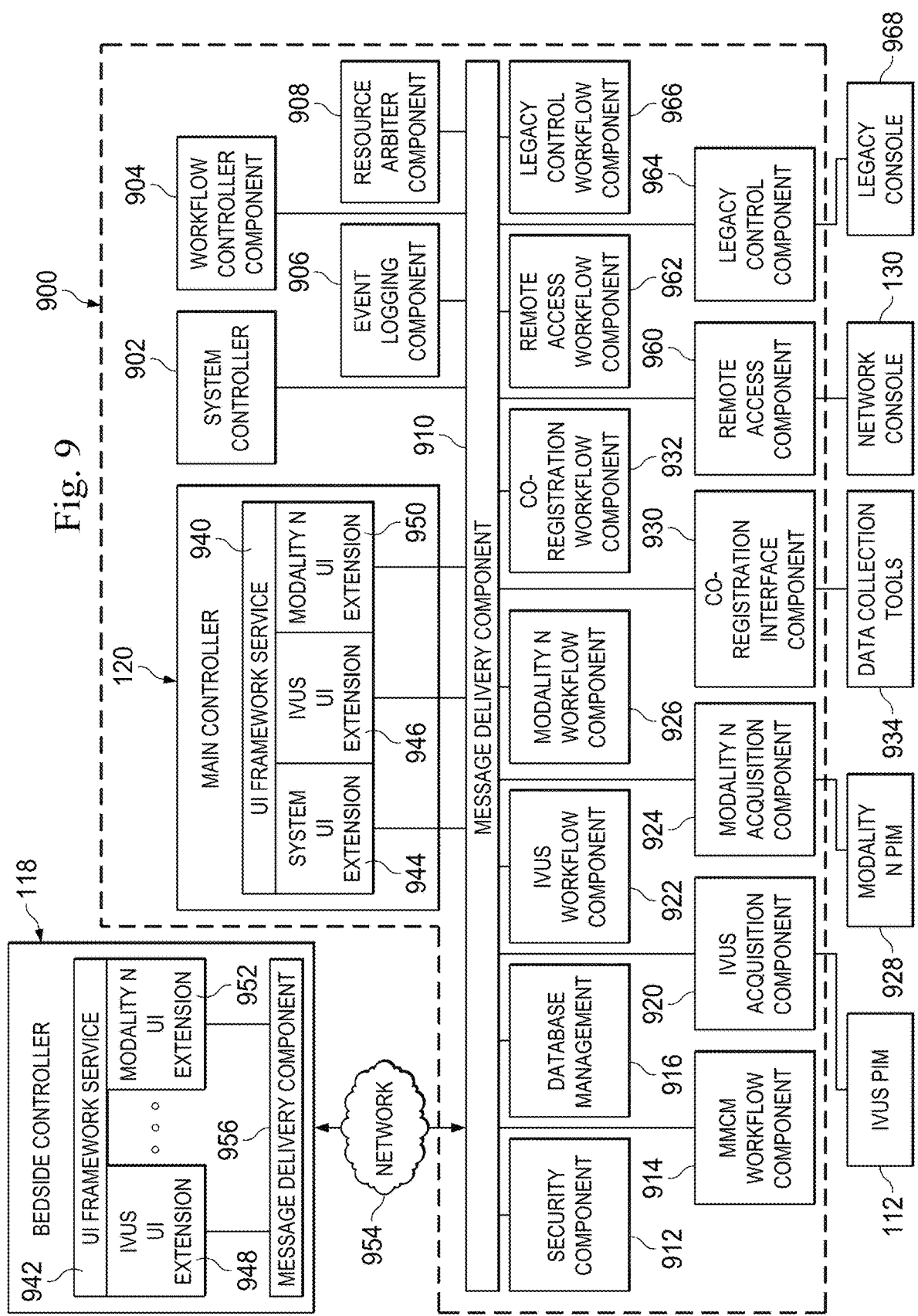
FIG. 9 is a functional block diagram of portions of the medical system of FIGS. 1A, 1B, and 1C according to some embodiments of the present disclosure.

With reference now to FIG. 9, illustrated is a functional block diagram of portions of the medical system 100 of FIGS. 1A, 1B, and 1C, including a processing framework 900 executing on some embodiments of the imaging system 101. The processing framework 900 includes various independent and dependent executable components that control the operation of the imaging system 101, including the acquisition, processing, and display of medical sensing data associated with one or more modalities. In general, the processing framework 900 of imaging system 101 is modular and extensible. That is, the framework 900 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 900 may be implemented as computer-executable instructions stored on a non-transitory computer-readable storage medium in the imaging system 101. In other instances, the processing framework 900 may be a combination of hardware and software modules executing within with the imaging system 101.

Generally, in the embodiment shown in FIG. 9, processing framework 900 includes a plurality of components that are configured to receive medical sensing data from one or more medical sensing devices, process the data, and output the data as diagnostic images via the main controller 120, the bedside controller 118, or other graphical display device. The framework 900 includes several system-level components that manage the core system functions of the imaging system 101 and also coordinate the plurality of modality-specific components. For instance, the framework 900 includes a system controller 902 that coordinates startup and shutdown of the plurality of executable components of the processing framework 900, including hardware and software modules related to acquisition and processing of patient diagnostic data. The system controller 902 is also configured to monitor the state of components executing within the framework 902, for instance, to determine if any components have unexpectedly stopped executing. In addition, the system controller 902 provides an interface through which other framework components may obtain system configuration and status information. Because the software framework 900 is modular, the system controller 902 is independent of the components within the framework that it manages so that errors and changes made to components do not affect the execution or structure of the system controller.

As mentioned above, the framework 900 is configured such that various extensions may be added and removed without system architecture changes. In certain embodiments, an extension executing within framework 900 may include a plurality of executable components that together implement the full functionality of the extension. In such embodiments, an extension may include an extension controller that is similar to the system controller 902 that is operable to startup, shutdown, and monitor the various executable components associated with the extension. For example, upon system startup, the system controller 902 may start an extension controller corresponding to a medical modality, and then the extension controller may, in turn, start the executable components associated with the modality. In one embodiment, extension controllers may be unallocated until system controller 902 associates them with a specific modality or other system task via parameters retrieved from a configuration mechanism, such as a configuration file.

The processing framework 900 further includes a workflow controller component 904 that is generally configured to govern the execution of the executable components of the framework 902 during medical sensing workflows. The workflow controller component 904 may govern workflows executed by the processing framework 900 in various different manners.

The processing framework 900 further includes an event logging component 906 that is configured to log messages received from various components of the processing framework. For instance, during system startup, the system controller 902 may send messages about the status of components being started to the event logging component 906 which, in turn, writes the messages to a log file in a standardized format. Additionally, the processing framework 900 includes a resource arbiter component 908 that is configured to manage the sharing of limited system resources between various executable components of the framework 902 during multi-modality medical sensing and/or treatment workflows. For example, during a multi-modality workflow, two or more components associated with different modalities within the processing framework 902 may be vying for the same system resource such as a graphical display on the main controller 120. The resource arbiter component 908 may coordinate sharing of limited system resources in various manners such as through a lock system, a queue system, or a hierarchical collision management system.

In one embodiment, the system controller 902, workflow controller component 904, event logging component 906, and resource arbiter component 908 may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 902 may be configured to alter the programmable logic within the FPGAs dynamically to implement various functionality needed at the time. As an aspect of this, the imaging system 101 may include one or more unassigned FPGAs that may be allocated by the system controller during system startup. For instance, if upon startup of the imaging system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality imaging system 101, the processing framework 900 further includes a message delivery component 910. In one embodiment, the message delivery component 910 is configured to receive messages from components within the framework 902, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 910 may be configured to receive messages from components within the framework 902, temporarily store the messages, and make the messages available for retrieval by other components within the framework (i.e., the message delivery component is a passive queue). In any case, the message delivery component 910 facilitates communication between executable components in the framework 900. For instance, the system controller 902 may utilize the message delivery component 910 to inquire into the status of components starting up during a system startup sequence, and then, upon the receiving status information, utilize the message delivery component to transmit the status information to the event logging component 906 so that it may be written to a log file. Similarly, the resource arbiter component 908 may utilize the message delivery component 910 to pass a resource token between components requesting access to limited resources.

In one example embodiment in which the message delivery component 910 is a passive queue, components in the framework 900 may packetize incoming medical sensing data into messages and then transmit the messages to a queue on the message delivery component where they may be retrieved by other components such as image data processing components. Further, in some embodiments, the message delivery component 910 is operable to make received messages available in a First-In-First-Out (FIFO) manner, wherein messages that arrive on the queue first will be removed from the queue first. In alternative embodiments, the message delivery component 910 may make messages available in a different manner for instance by a priority value stored in a message header. In one embodiment, the message delivery component 910 is implemented in random-access memory (RAM) in the imaging system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 910 may be accessed by software and hardware modules in imaging system 101 using Direct Memory Access (DMA).

The processing framework 902 may include a number of additional system components that provide core system functionality including a security component 912, a multi-modality case management (MMCM) component 914, and a database management component 916. In certain embodiments, the security component 912 is configured to provide various security services to the overall processing framework and to individual components. For example, components implementing an IVUS data acquisition workflow may utilize encryption application programming interfaces (APIs) exposed by the security component 912 to encrypt IVUS data before it is transmitted over a network connection. Further, the security component 912 may provide other security services, such as system-level authentication and authorization services to restrict access to the processing framework to credentialed users and also to prevent the execution of untrusted components within the extensible framework. The multi-modality case management (MMCM) component 914 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 916 is configured to present transparent database services to the other components in the framework 900 such that database connection and management details are hidden from the other components. For example, in certain embodiments, the database management component 916 may expose an API that includes database storage and retrieval functionality to components of the framework 900. In other words, a medical sensing workflow component may be able to transmit diagnostic data to a local and/or remote database such as a DICOM or PACS server via the database component without being aware of database connection details. In other embodiments, the database management component 916 may be operable to perform additional and/or different database services such as data formatting services that prepare diagnostic data for database archival.

As mentioned above, the processing framework 900 of the imaging system 101 is operable to receive and process medical data associated with one or a plurality of modalities. In multi-modal embodiments, the processing framework 900 includes a plurality of modular acquisition components and workflow components that are respectively associated with different medical sensing and diagnostic modalities. For instance, as shown in the illustrated embodiment of FIG. 9, the processing framework 900 includes an IVUS acquisition component 920 and an IVUS workflow component 922 that are respectively configured to receive and process IVUS medical sensing data from the IVUS PIM 112. In accordance with the modular and extensible nature of the processing framework 900, any number of additional acquisition and workflow components may be independently added to the framework as denoted by the modality "N" acquisition component 924 and the modality "N" workflow component 926 that acquire and process data from a modality "N" PIM 928. For example, in certain embodiments, the imaging system 101 may be communicatively coupled to the OCT PIM 114, the ECG system 116, a fractional flow reserve (FFR) PIM, an FL-IVUS PIM, and an ICE PIM. In other embodiments, additional and/or different medical sensing, treatment, or diagnostic devices may be coupled to the imaging system 101 via additional and/or different data communication connections known in the art. In such a scenario, in addition to the IVUS acquisition module 920, the processing framework 900 may include an FFR acquisition component to receive FFR data from an FFR PIM, an FL-IVUS acquisition component to receive FL-IVUS data from an FL-IVUS PIM, an ICE acquisition component to receive ICE data from an ICE PIM, and an OCT acquisition component is operable to receive OCT data from an OCT PIM. In this context, medical data communicated between the executable components of the processing framework 900 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the imaging system 101 such as devices associated with radiofrequency ablation (RFA), cryotherapy, or atherectomy and any PIMs or other control equipment associated with such treatment procedures. In such an embodiment, the modality "N" acquisition component 924 and the modality "N" workflow component 926 may be configured to communicate with and control the treatment devices such as by relaying control signals, relaying power levels, receiving device feedback, and receiving data collected by sensors disposed on the treatment devices.

In one embodiment, once the acquisition components 920 and 924 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 920 and 924 may be operable to manipulate the digitized medical sensing data in some way before it is transmitted to other portions of the framework 900. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 920 may identify and discard redundant IVUS data before it is passed on to save processing time in subsequent steps. The acquisition components 920 and 924 may additionally perform a number of tasks related to the acquisition of data including responding to interrupts generated by data buses (e.g., PCIe, USB), detecting which medical sensing devices are connected to imaging system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 922, receive unprocessed medical sensing and/or diagnostic data from respective acquisition components via the message delivery component 910. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 922 may interpret IVUS data received from the IVUS PIM 112 and convert the data into human-readable IVUS images. In one embodiment, a software stack within the framework may expose a set of APIs with which the workflow component 922 and other workflow components in the framework may call to access system resources such as the computational resources, the message delivery component 910, and communication resources. After processing acquired data, the modality-centric workflow components may transmit one or messages containing the processed data to other components within the framework 900 via the message delivery component 910. In some embodiments, before sending such messages, the components may insert a flag in the header indicating that the message contains processed data. Additionally, in some embodiments, after processing medical sensing data, the components may utilize the database management component 916 to transmit the processed data to archival systems such as a locally attached mass storage device or the network-based PACS server 127. In accordance with the modular architecture of the processing framework 900, the workflow components 922 and 926 are independent of each other and may be installed or removed without disrupting other components, and may be written by third parties. Further, due to their independence, they may be are operable to process signaling and imaging data from multiple medical sensing devices concurrently.

The processing framework 900 additionally includes a co-registration interface component 930 and a co-registration workflow component 932 that are configured to acquire and process data from any number of data collection tools 934 and co-register the acquired data with data acquired by one of the other acquisition components within the framework. In more detail, the co-registration interface component 930 may be operable to communicatively interface with medical data acquisition tools associated with any number of modalities, such as the ECG device 116 or the angiography system 117 of FIG. 1A. In certain embodiments, the interface component 930 may be operable to standardize and/or transform incoming modality data such that it may be co-registered with other sensing data acquired by the imaging system 101. As medical data is being acquired by the co-registration interface component 930, the co-registration workflow component 932 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 932 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 932 may register this position data against previously acquired MRI data. Still further, the co-registration workflow component 932 may facilitate co-registration of multi-modality data acquired by native acquisition components within the framework 900 such as the IVUS acquisition component 920 and modality "N" acquisition component 924. Additionally, in some embodiments, a real-time clock may be integrated into the co-registration workflow component 932. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1A, a clinician utilizing the imaging system 101 may control workflows and view diagnostic images through the main controller 120 and the bedside controller 118. The main controller 120 and the bedside controller 118 respectively include user interface (UI) framework services 940 and 942 that support a plurality of user interface (UI) extensions (or components). In general, the UI extensions supported by the UI framework services 940 and 942 respectively correspond to medical sensing modalities and are operable to render a user interface for control of the associated acquisition workflow and display of processed sensing data. Similar to the processing framework 900, the UI frameworks 940 and 942 are extensible in that they support UI extensions that are independent of one another. That is, its modular design allows the UI frameworks 940 and 942 to be extended to accommodate additional medical sensing modality user interfaces without impacting existing user interfaces or requiring changes to the underlying UI architectures. In the illustrated embodiment, the main controller 120 includes a system UI extension 944 that renders a user interface containing core system controls and configuration options. For example, a clinician may startup, shutdown or otherwise manage the imaging system 101 using the user interface rendered by the system UI extension 944. In one embodiment, the components of the main controller 120 may be considered part of the processing framework 900. The IVUS UI extensions 946 and 948 render user interfaces for the main controller 120 and bedside controller 118, respectively. For example, the IVUS UI extensions 946 and 948 may render and display the touch screen buttons used to control an IVUS workflow and also render and display the IVUS diagnostic images created by the IVUS workflow component 922. Similarly, the modality "N" UI extensions 950 and 952 render controls and images associated with a modality "N" workflow.

In one embodiment, the UI framework services 940 and 942 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 940 and 942 may include a multi-tasking framework to coordinate concurrently executing UI extensions. For instance, in the event the imaging system 101 is simultaneously acquiring data associated with more than one modality, the UI framework services 940 and 942 may present the user with a modality selector screen on which a desired user interface may be selected.

The UI framework service 940 communicates with the components of the processing framework 900 via the message delivery component 910. As shown in the illustrated embodiment of FIG. 9, the bedside controller 118 may be communicatively coupled to the processing framework 900 via a network connection 954. The network connection 954 may be any type of wired of wireless network connection such as an Ethernet connection or IEEE 802.11 Wi-Fi connection. Alternatively, one or both of the main and bedside controllers 120 and 118 may communicate with the processing framework 900 via a local bus connection such as a (PCIe) data bus connection, a USB connection, a Thunderbolt connection, a FireWire connection, or some other high-speed data bus connection. Further, in the illustrated embodiment of FIG. 9, the bedside controller includes a message delivery component 956 that is configured to facilitate message-based communication between the UI extensions in the bedside controller 118 and the components in the processing framework 900. In certain embodiments, the message delivery component 956 may extract diagnostic image data from network communication packets as they arrive over the network connection 954.

The processing framework 900 includes additional components that allow a clinician to access and/or control workflows executing in the multi-modality imaging system 101. For example, the framework 900 includes a remote access component 960 that communicatively couples the network console 130 (FIG. 1A) to the processing framework 900. In one embodiment, the remote access component 960 is operable to export control functionality of the imaging system 101 to the network console 130, so that the network console may present workflow control functions in its user interface. In certain embodiments, the remote access component 960 may receive workflow commands from the network console 130 and forward them to a remote access workflow component 962. The remote access workflow component 962 may dictate the set of commands and diagnostic data to which a remote user may access through the network console 130. Further, the legacy control component 964 and legacy control workflow component 966 provide some level of access to modality workflow control and data to users of legacy consoles 968 (e.g. button consoles, mice, keyboards, standalone monitors).

In one embodiment, the core system components of the processing framework 900 and the additional components such as the modality-related components may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 900 of FIG. 9 is simply an example embodiment and, in alternative embodiments, the framework may include different and/or additional components configured to carry out various medical sensing workflows. For instance, the processing framework 900 may further include executable components configured for the evaluation of a stenosis of a human blood vessel or configured to facilitate control of computer-assisted surgery or remotely-controlled surgery.

Figure 10:
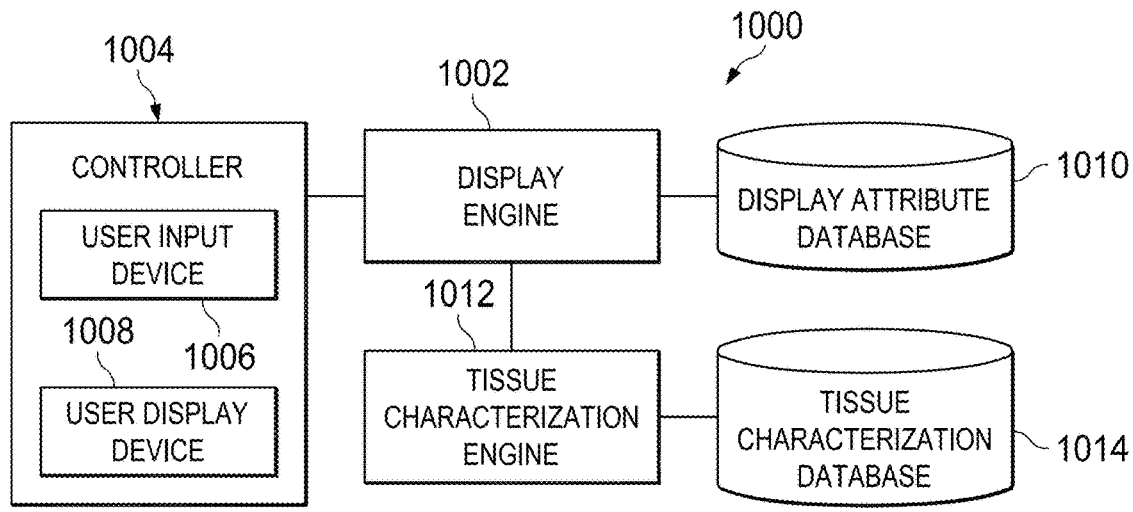
FIG. 10 is a functional block diagram of portions of the medical system of FIGS. 1A, 1B, and 1C including a user interface component for configuring the display of medical sensing data according to some embodiments of the present disclosure.

Referring now to FIG. 10, illustrated is a functional block diagram of portions of the medical system 100 of FIGS. 1A, 1B, and 1C including a user interface component 1000 for configuring the display of medical sensing data according to some embodiments of the medical system 100. In general, the user interface component 1000 receives display attributes from a user and, based on the attributes, controls the acquisition, processing, and/or presentation of the medical data. In this way, the user interface component 1000 allows operators to zero in on relevant data, to reduce screen clutter, and to improve the quality of displayed data. The user interface component 1000 can also conserve system resources by selectively processing only the data to be displayed. This efficiency can improve system responsiveness and user experience.

The user interface component 1000 includes a display engine 1002 that presents a set of display controls to a user and receives a user-selected display attribute. Accordingly, the display engine 1002 is communicatively coupled to a controller 1004, which includes a user input device 1006 and a user display device 1008. Examples of suitable user input devices 1006 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and/or other user input devices known to one of skill in the art.

In addition to receiving display attributes directly from the user, the display engine 1002 may also receive display attributes from a database. In some such embodiments, the user interface component 1000 further includes a display attribute database 1010 communicatively coupled to the display engine 1002. The display engine 1002 utilizes the display attribute database 1010 to save and restore display attributes, to edit attributes, and to create and distribute new attributes.

The display attribute governs the presentation of the data to the user. As disclosed above, a multi-modality imaging system (e.g., imaging system 101) may receive sets of medical sensing data collected from a number of individual sensors and corresponding to a wide array of sensing modalities including pressure data, flow data, IVUS data, photoacoustic IVUS data, FL-IVUS data, FFR determinations, CFR determinations, OCT data, transesophageal echocardiography data, image-guided therapy data, other suitable medical data, and/or combinations thereof. In various embodiments, the received display attribute applies to a portion of the available medical data, multiple portions of the medical data, and/or all of the medical data. Accordingly, the display attribute may specify the portion of the medical data to which it is to be applied. The display attribute may specify the applicable dataset by sensor, by sensing instrument, by modality, by a window of time, by other suitable divisions and/or by combinations thereof, and the display attribute may modify the specified dataset independent of other datasets received by the system. Thus, in an embodiment, a display attribute specifies a display characteristic for data collected by a first, relatively proximal, sensor independent of data collected by a second, relatively distal, sensor despite that both sensors are incorporated into a single sensing instrument. In another embodiment, a display attribute specifies a display characteristic for data of a first modality independent of data of a second modality despite that both datasets are collected by a single physical sensor. This can be extended to other suitable divisions.

The display attribute may include static values as well as dependent or dynamic values. For example, a display attribute may specify a value that depends on another parameter or data value. In some exemplary embodiments, the display attributes may specify values that depend on user preferences, an operative course of a medical procedure being performed, patient information, the subset of data to which the display attribute applies, a subset of data independent of the display attribute, a status indicator, and/or a sensor attribute. In one such embodiment, the display attribute specifies a set of values that the display engine 1002 selects between based on the hospital or surgical facility performing the procedure. In another such embodiment, the display attribute specifies physician-specific values.

Based on the display attribute, the display engine 1002 generates a set of instructions to govern the acquisition, processing, and display of the applicable data. With respect to data acquisition instructions, the instructions may direct the operation of sensors, sensing instruments, supporting devices such as a PIM or imaging system, and/or other data processing components. Exemplary instructions designate sensor operating power, amplifier gain, and/or any other applicable operating parameter. In some embodiments, a generated instruction halts or prevents the collection of data. To reduce power, system load, and potential signal interference, in some such embodiments, halting includes disabling or powering down the sensor (e.g., ultrasound transducer, pressure sensor, flow meter, OCT sensor, etc.), corresponding interface components, processing components, and/or other related components when the display attribute signals that the sensor data will not be displayed. In some embodiments utilizing optical sensors, halting includes disabling or powering down a corresponding laser emitter.

With respect to data processing instructions, the generated instructions may direct the operation of sensors, sensing instruments, supporting devices such as a PIM or imaging system, and/or other data processing components. Exemplary instructions designate a sampling rate, a baseline correction factor, an IVUS focusing parameter, a pseudo-color conversion scheme, and/or another applicable operating parameter. In one such example, the generated instructions activate a motion detection algorithm, such as blood flow analysis, and specify one or more IVUS transducer to supply the data.

With respect to the display of the processed data, the instructions may likewise direct the operation of sensors, sensing instruments, supporting devices such as a PIM or imaging system, and/or other data processing components.

The display engine 1002 provides the generated instructions to the respective components of the medical system 100 including the sensors, the sensing instruments, the supporting devices, and/or other data processing components. For example, in some embodiments, the display engine 1002 provides instructions based on the display attribute to a tissue characterization engine 1012. In brief, tissue characterization processes such as Virtual Histology™ (a trademark of Volcano Corporation) compare received medical sensing data against data collected from known samples in order to identify constituent tissues and structures. Recognized tissues may be highlighted upon display using color, markers, outlines, and other signifiers for easy identification by the operator. U.S. Pat. No. 7,074,188, entitled "SYSTEM AND METHOD OF CHARACTERIZING VASCULAR TISSUE, U.S. Pat. No. 7,175,597, entitled "NON-INVASIVE TISSUE CHARACTERIZATION SYSTEM AND METHOD," and U.S. Pat. No. 7,988,633, entitled "APPARATUS AND METHOD FOR USE OF RFID CATHETER INTELLIGENCE," disclose tissue characterization in greater detail and are hereby incorporated by reference in their entirety. Using the display engine 1002, operators can control the display of recognized tissues in order to highlight important structures and to reduce overall clutter. In some embodiments, the display engine 1002, by specifying a subset of the total data for the tissue characterization engine 1012 to analyze or exclude, improves characterization speed and frees resources for other types of image processing.

Thus, in some embodiments, the display engine 1002 supports display attributes that relate to tissue characterization. Such display attributes may specify the dataset and/or the tissues (e.g., thrombus, plaque, adventitia, fibrous tissue, fibro-lipidic tissue, calcified necrotic tissue, calcific tissue, collagen composition, cholesterol, stent, vessel wall, etc.) to which the attributes apply. In an exemplary embodiment, a display attribute specifies that the attribute applies to data collected by a particular sensor and to plaque structures identified therein. In a further exemplary embodiment, a display attribute specifies that the attribute applies to IVUS sensor data and applies to all structures except stents.

The display engine 1002 may therefore support a number of display attributes that are particularly relevant to tissue characterization. For example, a display attribute may specify a threshold value, an identifier (e.g., color, marker shape, outline, etc.) to associate with a tissue type, whether to hide, display, or dim particular tissue types, and/or may specify other relevant tissue characterization parameters. Display attributes may include dependent or dynamic values in addition to static values. Based on the display attribute, the display engine 1002 generates a set of instructions to govern the tissue characterization process and the display of characterized data. These instructions may be executed by the tissue characterization engine 1012 and/or other suitable components of the medical system 100 including the imaging system 101.

In addition to providing instructions to other components, in some embodiments, the display engine 1002 further executes one or more of the generated instructions during the display of the relevant sensing data. In one such embodiment, the display engine 1002 executes an instruction that specifies a pseudo-color scheme during a conversion of signal intensity into a color value. The display engine 1002 then presents the converted pseudo-color data at the user display device 1008. In a further such embodiment, the display engine 1002 executes an instruction that adjusts the contrast of an identified subset of an IVUS image corresponding to a hot spot produced by a stent. The display engine 1002 then presents the adjusted IVUS image at the user display device 1008. In a further such embodiment, the display engine 1002 maintains a tissue characterization identifier table based on the instructions generated in response to the display attributes. When displaying characterized sensing data, the display engine 1002 applies identifiers from the table to highlight identified tissues.

Portions of the user interface component 1000 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 1000 are incorporated into components of the medical system 100 described with reference to FIGS. 1A, 1B, and 1C and FIGS. 2-9. For example, in some such embodiments, controller 1004 is a component of a bedside controller 118, a main controller 120, a boom display 122, and/or a network console 130 described with reference to FIG. 1A. As a further example, in some such embodiments, the display engine 1002 is incorporated into a UI framework service 940 of a main controller 120, a UI framework service 942 of a bedside controller 118, and/or a UI extension such as IVUS UI extension 946 or IVUS UI extension 948 described with reference to FIG. 9. In other embodiments, the user interface component 1000 is a separate and distinct component of the multi-modality medical system 100.

One of ordinary skill in the art will recognize that the above examples of display attributes and instructions are merely exemplary embodiments and are not limiting. In further embodiments, the display engine 1002 receives further types of display attributes and provides additional functionality allowing users to tailor the display to their liking.

Figure 11:
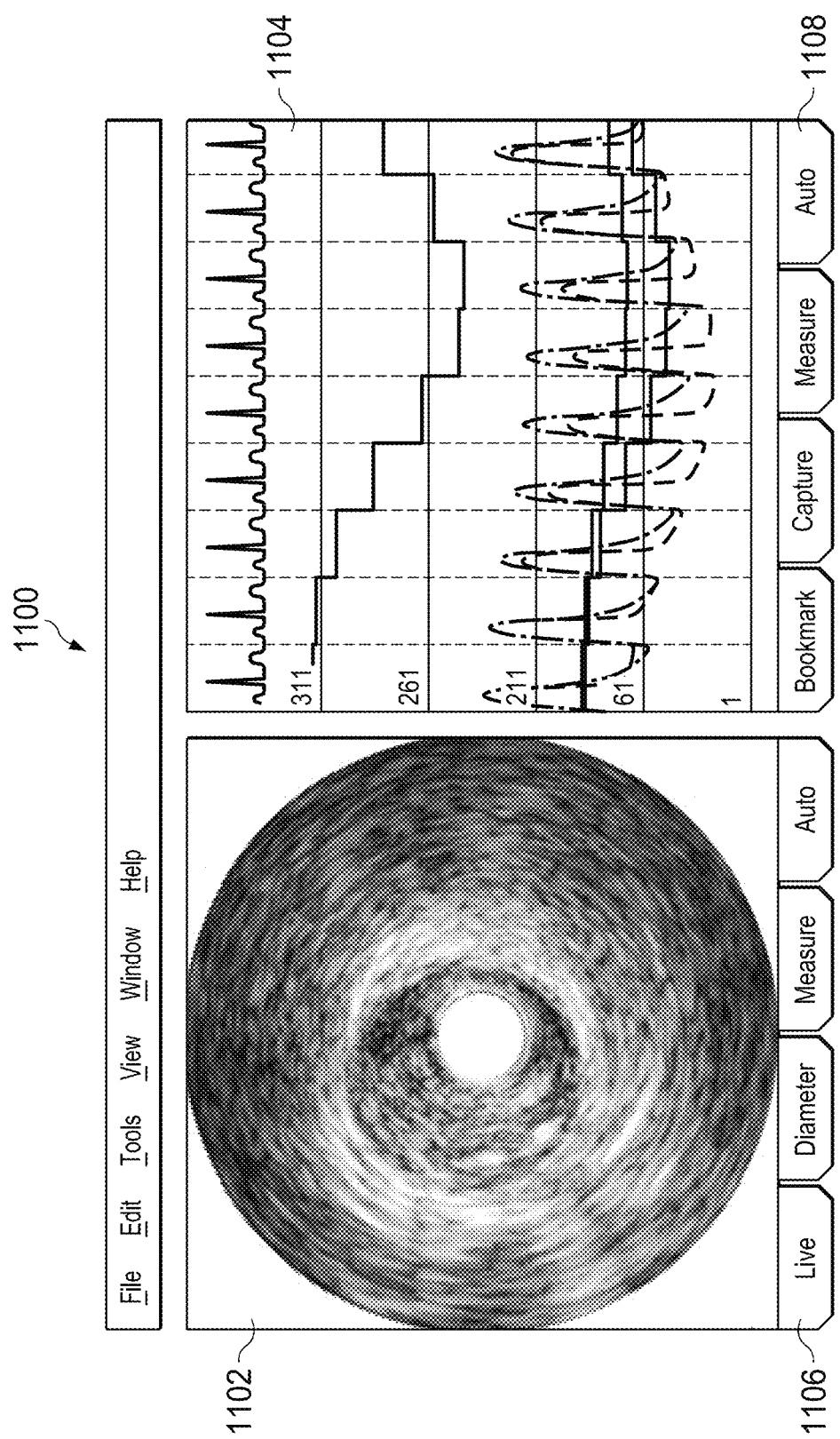
FIG. 11 is a diagram of an exemplary user interface for customizing the display of multi-modality medical data according to some embodiments of the present disclosure.

FIG. 11 is a diagram of an exemplary user interface 1100 for customizing the display of multi-modality medical data according to some embodiments of the present disclosure. The user interface 1100 may be displayed on a user display such as the user display 1008 described with reference to FIG. 10. The user interface 1100 represents one possible arrangement for displaying the information presented by the multi-modality processing system 100 and more specifically presented by the display engine 1002. One skilled in the art will recognize that alternate arrangements are both contemplated and provided for.

In the illustrated embodiment, the user interface 1100 includes one or more display panes 1102 and 1104 for displaying medical sensing data corresponding to one or more modalities. Examples of medical sensing data include IVUS data, forward-looking IVUS data, flow velocity, pressure data, FFR determinations, CFR determinations, OCT data, and trans-esophageal echocardiography data. In the illustrated embodiment, pane 1102 displays a first subset of data corresponding to a first modality, and pane 1104 displays a second subset of data corresponding to a second modality. The first and second modalities may be different. The user interface 1100 allows the user to select independent display attributes for the first subset of data of pane 1102 and the second subset of data of pane 1104. Display attribute options may be presented via checkboxes, exclusive and non-exclusive lists, radio buttons, and/or other suitable interface schemes. In the illustrated embodiment, display attributes for the first subset of data of pane 1102 are presented via tabs 1106 and display attributes for the second subset of data of pane 1104 are presented via tabs 1108, although this is merely exemplary and other arrangements including dropdown menus, toolbars, trees, and other suitable arrangements are provided for. Upon user selection of a display attribute, the display attribute is applied to the corresponding data subset or subsets and the display 1100 is updated accordingly.

Figure 12:
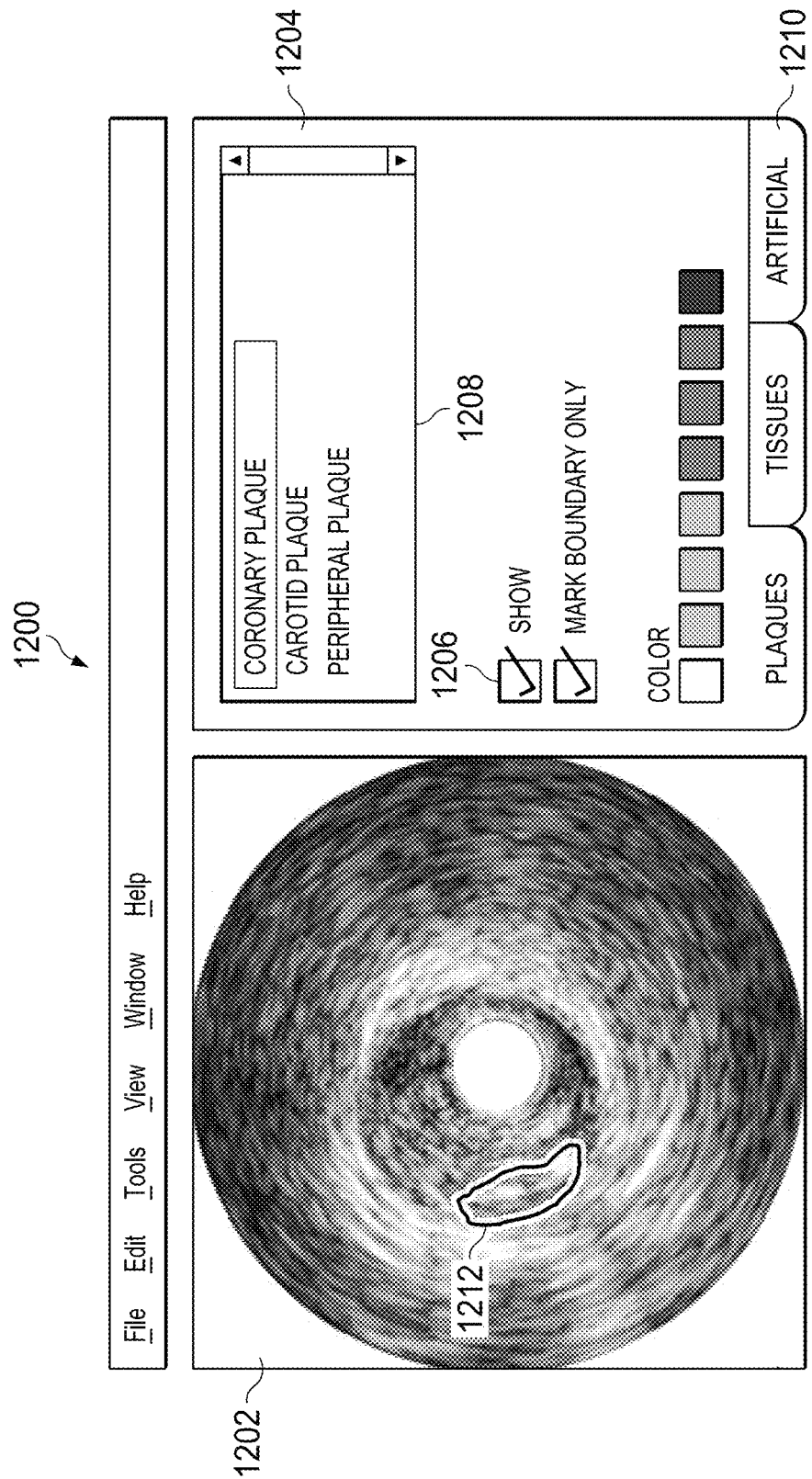
FIG. 12 is a diagram of an exemplary user interface for customizing the display of characterized tissue according to some embodiments of the present disclosure.

FIG. 12 is a diagram of an exemplary user interface 1200 for customizing the display of characterized tissue according to some embodiments of the present disclosure. The user interface 1200 may be displayed on a user display such as the user display 1008 described with reference to FIG. 10. The user interface 1200 represents one possible arrangement for displaying the information presented by the multi-modality processing system 100 and more specifically presented by the display engine 1002. One skilled in the art will recognize that alternate arrangements are both contemplated and provided for.

In the illustrated embodiment, the user interface 1200 includes one or more display panes 1202 for displaying medical sensing data corresponding to one or more modalities. The user interface 1200 may also include one or more display attribute panes 1204. The display attribute pane 1204 presents user-selectable display attributes corresponding to a tissue characterization process via checkboxes 1206, exclusive and non-exclusive lists 1208, radio buttons, and other suitable interface schemes. In the illustrated embodiment, the display attribute pane 1204 presents the display attribute options in categories presented as tabs 1210, although this is merely exemplary and other arrangements including dropdown menus, toolbars, trees, and other suitable arrangements are provided for. Upon user selection of display attribute, the display attribute is applied to the corresponding data and the display is updated. This may include updating a tissue marker (e.g., marker 1212).

As disclosed above in detail, a medical imaging system (e.g., imaging system 101 of FIG. 1A) receives, directs, processes, and displays medical sensing data. The medical imaging system may receive considerable amounts of data collected from a number of individual sensors and corresponding to a wide array of sensing modalities. For example, in various embodiments, the medical imaging system receives pressure data, flow data, IVUS data, photoacoustic IVUS data, FL-IVUS data, FFR determinations, CFR determinations, OCT data, transesophageal echocardiography data, image-guided therapy data, other suitable medical data, and/or combinations thereof. To assist users in sifting through this wealth of information, the medical imaging system may adjust the collection, processing, and display of the underlying data at the user's command. Methods of responding to these display attributes are disclosed with reference to FIGS. 13-15.

Figure 13:
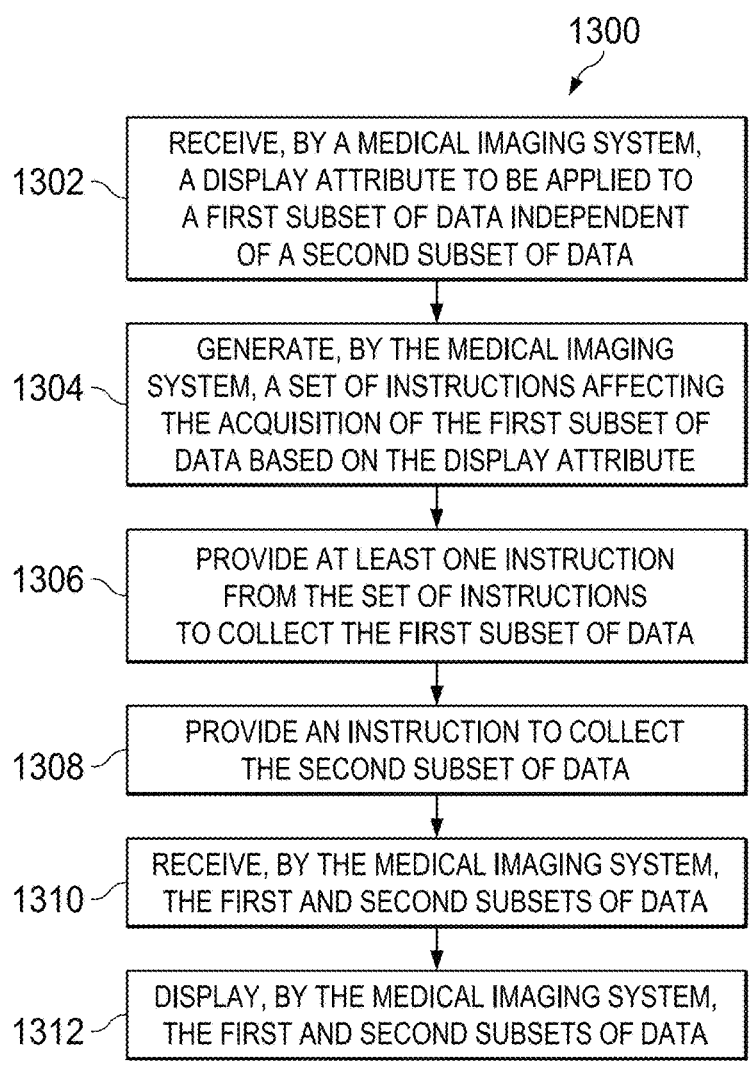
FIG. 13 is a flow diagram of a method of collecting medical sensing data based on a display attribute according to some embodiments of the present disclosure.

FIG. 13 is a flow diagram of a method 1300 of collecting medical sensing data based on a display attribute according to some embodiments of the present disclosure. It is understood that additional steps can be provided before, during, and after the steps of method 1300, and some of the steps described can be replaced or eliminated for other embodiments of the method. Referring to block 1302 of the method 1300, the medical imaging system receives the display attribute. The display attribute may be received via a user input and/or an external storage resource such as a display attribute database. The display attribute governs the presentation of the data to the user. The display attribute may be applied to a single data subset, multiple data subsets, and/or all the available medical data. Accordingly, in the embodiments of FIG. 13, the display attribute is applied to a first data subset, but not necessarily a second data subset. First and second subsets may be defined by sensor, by sensing instrument, by modality, by a window of time, by other suitable divisions and/or by combinations thereof. In some embodiments, the display attribute specifies the subsets to which it is to be applied.

The display attribute may include static values, dynamic values, and/or dependent values. In some exemplary embodiments, the display attributes may specify values that depend on user preferences, an operative course of a medical procedure being performed, a medical facility performing the procedure, patient information, the subset of data to which the display attribute applies, a subset of data independent of the display attribute, a status indicator, and/or a sensor attribute.

In block 1304, the medical system generates a set of instructions to govern the acquisition of the first data subset based on the display attribute. In some embodiments, the instructions designate sensor operating power, amplifier gain, and/or any other applicable operating parameter. In some embodiments, a generated instruction halts or prevents the collection of data, which may include disabling an associated sensor and, in the case of optical sensors, may include disabling a corresponding laser emitter. In some embodiments, a generated instruction causes data to be collected and stored but not processed in real-time. This frees up real-time resources while ensuring that the data is available for later evaluation. In block 1306, at least one instruction of the set is provided in order to collect the first data subset according to the display attribute. In various exemplary embodiments, the instruction is provided to a component of the medical system such as a sensor (e.g., ultrasound transducer, pressure sensor, flow sensor, OCT sensor, etc.), a sensing instrument (e.g., catheter, guide catheter, guide wire, etc.), a supporting device such as a PIM or an imaging system, and/or other data acquisition component.

In block 1308, an instruction is provided in order to collect the second data subset. The instruction to collect the second data subset is independent of the display attribute. In block 1310, the set of medical data including the first and second subsets, the first being collected according to the display attribute is received by the medical system. In block 1312, the set of medical data is displayed according to the display attribute.

Figure 14:
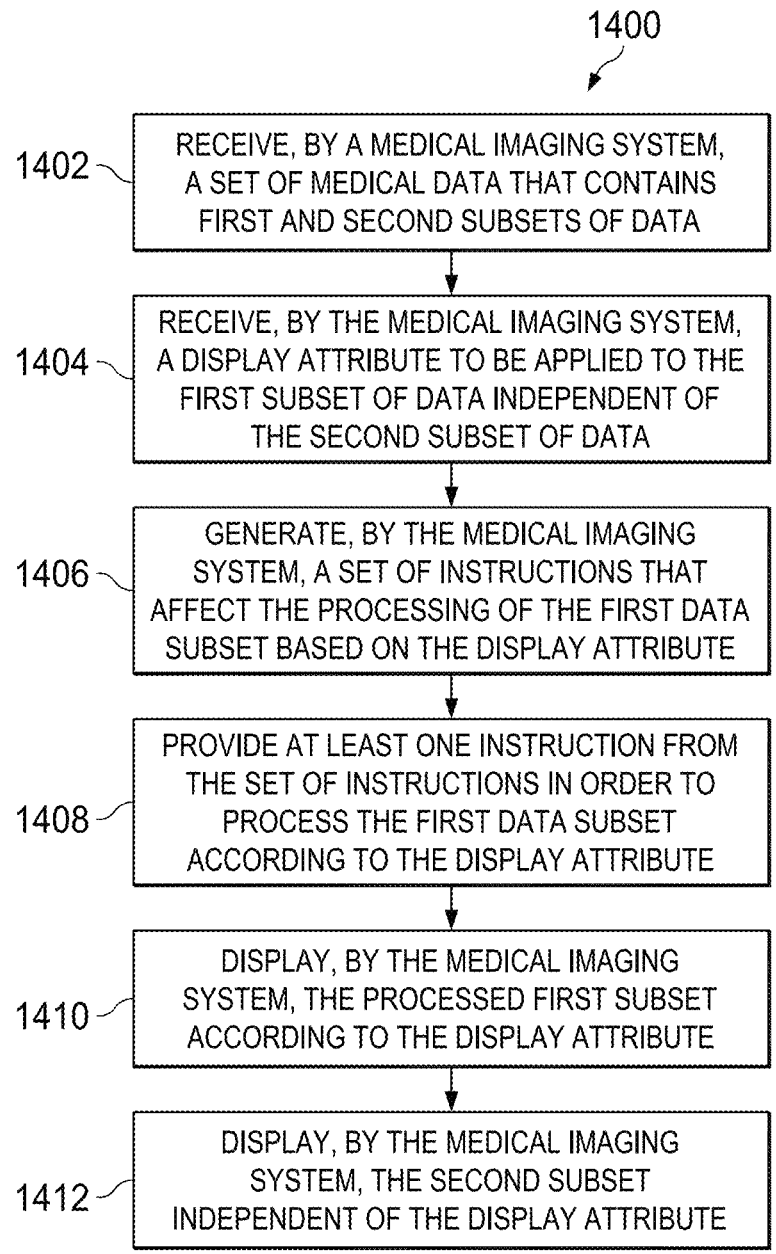
FIG. 14 is a flow diagram of a method of processing and displaying medical sensing data based on a display attribute according to some embodiments of the present disclosure.

FIG. 14 is a flow diagram of a method 1400 of processing and displaying medical sensing data based on a display attribute according to some embodiments of the present disclosure. It is understood that additional steps can be provided before, during, and after the steps of method 1400, and some of the steps described can be replaced or eliminated for other embodiments of the method. In block 1400, a medical imaging system receives a set of medical data that contains first and second subsets of data. Data subsets may be defined by sensor, by sensing instrument, by modality, by a window of time, by other suitable divisions and/or by combinations thereof.

In block 1404, the medical imaging system receives a display attribute. The display attribute may be applied to a single data subset, multiple data subsets, and/or all available medical data. Accordingly, in the embodiments of FIG. 14, the display attribute is applied to the first data subset, but not necessarily the second data subset. In some embodiments, the display attribute specifies the subsets of the set of medical data to which it is to be applied.

The display attribute governs the presentation of data to the user. The display attribute may include static values, dynamic values, and/or dependent values. In some exemplary embodiments, the display attributes specify values that depend on user preferences, an operative course of a medical procedure being performed, a medical facility performing the procedure, patient information, the subset of data to which the display attribute applies, a subset of data independent of the display attribute, a status indicator, and/or a sensor attribute.

In block 1406, the medical system generates a set of instructions that affect the processing of the first data subset based on the display attribute. In some exemplary embodiments, the instructions designate a threshold value, a pseudo-color conversion scheme, and a display state from the group consisting of a shown state, a dimmed state, and a hidden state. In block 1408, at least one instruction of the set is provided in order to process the first data subset according to the display attribute. In various exemplary embodiments, the instruction is provided to a component of the medical system such as a sensor (e.g., ultrasound transducer, pressure sensor, flow meter, OCT sensor, etc.), a sensing instrument (e.g., a catheter, guide catheter, guide wire, etc.), a supporting device such as a PIM or an imaging system, and/or other data acquisition component.

In block 1410, the medical system displays the first subset according to the display attribute, and, in block 1412, the medical system displays the second subset independent of the display attribute.

Figure 15:
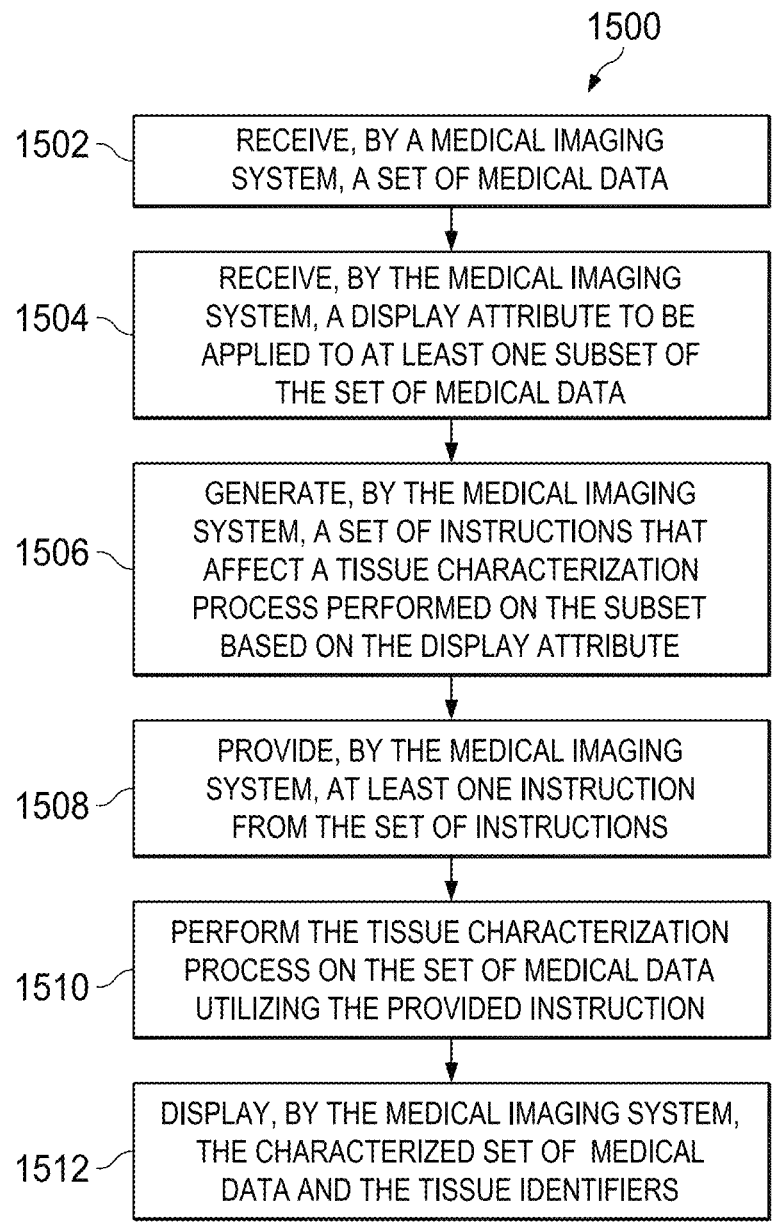
FIG. 15 is a flow diagram of a method of performing tissue characterization based on a display attribute according to some embodiments of the present disclosure.

FIG. 15 is a flow diagram of a method 1500 of performing tissue characterization based on a display attribute according to some embodiments of the present disclosure. It is understood that additional steps can be provided before, during, and after the steps of method 1500, and some of the steps described can be replaced or eliminated for other embodiments of the method. In block 1502, a medical imaging system receives a set of medical data. The set may include various subsets corresponding to disparate sensors, modalities, and/or sensing instruments.

In block 1504, the system receives a display attribute to be applied to at least one subset of the medical data. The display attribute may also apply to select tissues to be characterized while not necessarily applying to other tissue types. Accordingly, such display attributes may specify the dataset and/or the tissues (e.g., thrombus, plaque, adventitia, fibrous tissue, fibro-lipidic tissue, calcified necrotic tissue, calcific tissue, collagen composition, cholesterol, stent, vessel wall, etc.) to which the attributes apply. Additionally, the display attribute may include static values, dynamic values, and/or dependent values. In block 1506, the medical system generates a set of instructions based on the display attribute for use in a tissue characterization process to be performed on the set of medical data. For example, the instructions may specify a threshold value, an identifier (e.g., color, marker shape, outline, etc.) to associate with a tissue type, whether to hide, display, or dim particular tissue types, and/or may specify other relevant tissue characterization parameters.

In block 1508, at least one instruction of the set is provided for use in the tissue characterization process. In various exemplary embodiments, the instruction is provided to a component of the medical system such as a sensor (e.g., ultrasound transducer, pressure sensor, flow meter, OCT sensor, etc.), a sensing instrument (e.g., a catheter, guide catheter, guide wire, etc.), a supporting device such as a PIM or an imaging system, and/or other data acquisition component. In block 1510, the tissue characterization process is performed using the provided instruction. The tissue characterization process identifies constituent tissue elements from the medical data and assigns tissue identifiers to the constituent tissue elements to identify them upon display. In block 1512, the medical system displays the characterized set of medical data and the tissue identifiers.

Figure 16:
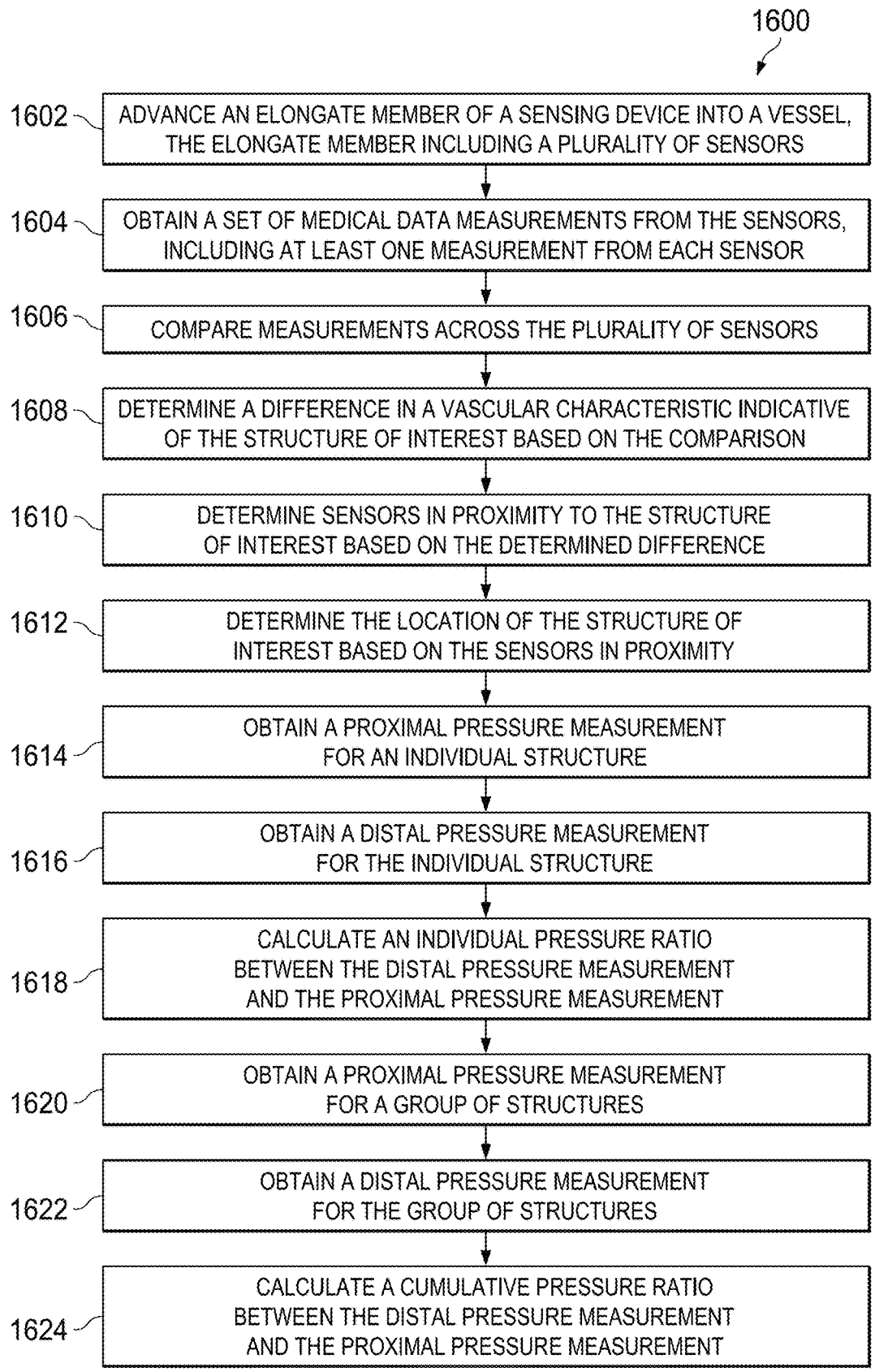
FIG. 16 is a flow diagram of a method of locating a structure within a vessel according to some embodiments of the present disclosure.

FIG. 16 is a flow diagram of a method 1600 of locating a structure within a vessel according to some embodiments of the present disclosure. It is understood that additional steps can be provided before, during, and after the steps of method 1600, and some of the steps described can be replaced or eliminated for other embodiments of the method. In block 1602, a flexible elongate member (e.g., catheter, guide catheter, guide wire, etc.) of a sensing device is advanced into a vessel. The elongate member incorporates a plurality of sensors disposed along a longitudinal length of the elongate member. The plurality of sensors may include any suitable medical sensors such as ultrasound transducers, photoacoustic ultrasound transducers, pressure sensors, optical pressure sensors, flow sensors, optical flow sensors, OCT transceivers, and/or other suitable sensors, and the associated sensors may correspond to one or more modalities including, flow, optical flow, IVUS, photoacoustic IVUS, FL-IVUS, pressure, optical pressure, fractional flow reserve (FFR) determination, coronary flow reserve (CFR) determination, optical coherence tomography (OCT), transesophageal echocardiography, image-guided therapy, other suitable modalities, and/or combinations thereof.

In block 1604, a set of medical data measurements are obtained. The set includes at least one measurement from each sensor of the plurality of sensors. In block 1606, the measurements are compared across the plurality of sensors. Comparing may include direct comparison between sensors, comparison to a reference value such as those in a tissue characterization database, comparison to a threshold, and/or other types of comparisons. In some embodiments, comparing includes performing a series of FFR calculations and comparing the FFR ratios to a threshold that suggests that a stenosis lies between the proximal and distal sensors. In some embodiments, comparing includes comparing IVUS and/or OCT measurements to a tissue characterization database to detect one or more of a thrombus, a plaque, adventitia, fibrous tissue, fibro-lipidic tissue, calcified necrotic tissue, calcific tissue, collagen composition, cholesterol, a stent, a vessel wall, and/or other structure. In block 1608, the comparison is used to detect a difference in a vascular characteristic indicative of the structure of interest. The difference may be an FFR ratio beyond a threshold, a variation in tissue, a difference in signal intensity or character, and/or other suitable differences. In block 1610, the difference is used to determine the sensors in proximity to the structure of interest. For example, in the case of an FFR ratio, the sensors in proximity may include the sensors involved in the ratio calculation. In the case of a structure recognized via a tissue characterization process, the sensors in proximity may include the sensors that collected the characterized data from which the structure was recognized. In block 1612, the location of the structure is determined based on the sensors in proximity.

In some embodiments, once the structure is located, further diagnostic analysis may be performed. In one such embodiment, individual and cumulative effects of a plurality of stenoses are measured and analyzed. In block 1614, a proximal pressure measurement is obtained for each stenosis of the plurality of stenoses. The proximal measurement is obtained from a sensor proximal to the stenosis and substantially between the stenosis and any stenosis that happens to be proximal to the one being measured. In block 1616, a distal pressure measurement is obtained for the stenosis using a sensor distal to the stenosis and substantially between the stenosis and any subsequent distal stenosis. In block 1618, an individual pressure ratio is determined for the stenosis using the collected distal and proximal sensor measurements.

In block 1620, a proximal pressure measurement for determining a cumulative effect is obtained utilizing a sensor proximal to all of the stenoses of the plurality of stenoses. In block 1622, a corresponding distal pressure measurement is obtained using a sensor distal to all of the stenoses of the plurality of stenoses. In block 1624, a cumulative pressure ratio is determined for the plurality using the collected distal and proximal sensor measurements.

In some embodiments, this further diagnostic analysis includes repositioning a detailed sensing region of the elongate member to be adjacent to the structure of interest. In an embodiment, this includes adjusting the location of the elongate member of the vessel. The amount by which the elongate member is advanced or withdrawn may be determined based on the difference between the location of the structure determined in block 1612 and the location of the detailed sensing region. Once the detailed sensing region is positioned, subsequent measurements are obtained using the sensors disposed within the detailed sensing region. The subsequent measurements may correspond to a different modality than the previous measurements. For example, in an embodiment, pressure measurements are used to locate a stenosis, and IVUS measurements are used to examine the stenosis in detail. In another exemplary embodiment, structural IVUS measurements are used to locate a bifurcation, and Doppler IVUS measurements are used to examine the bifurcation in detail.

Figure 17:
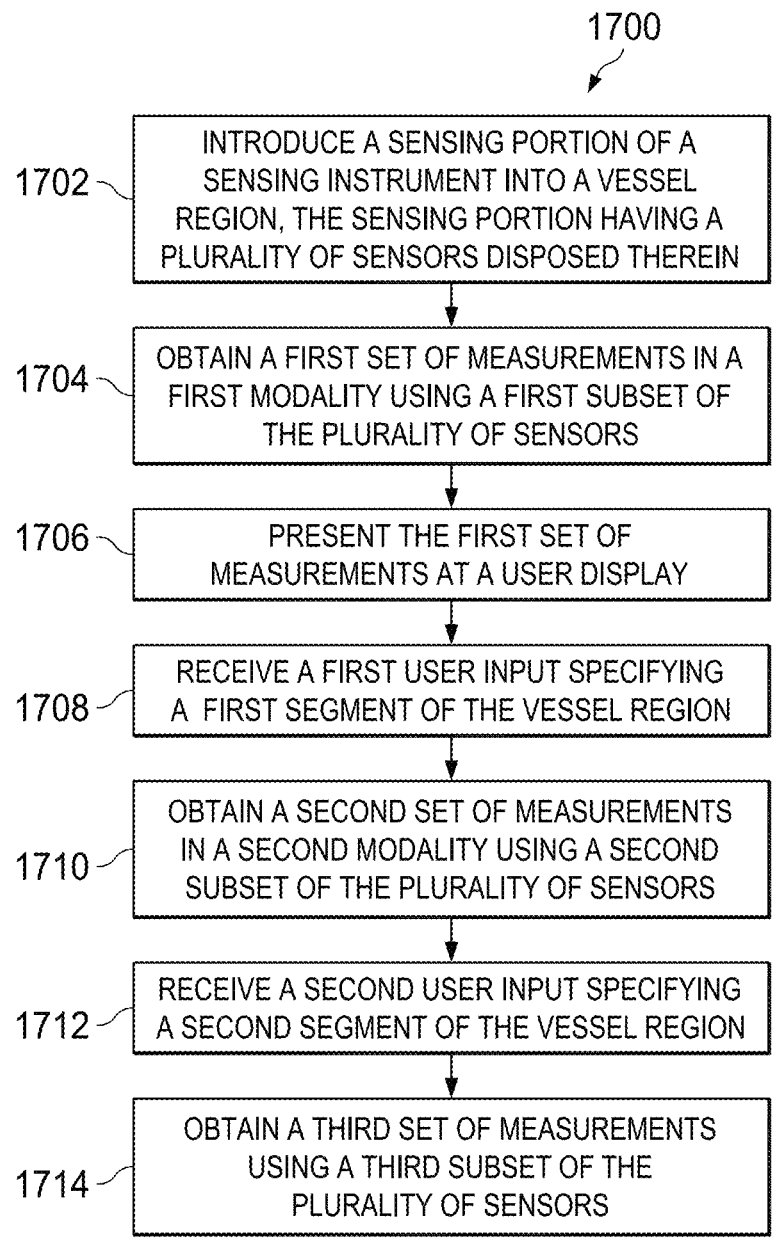
FIG. 17 is a flow diagram of a method of evaluating a vessel according to some embodiments of the present disclosure.

Referring now to FIG. 17, in some embodiments, detailed measurements along the length of a vessel may be made without repositioning the elongate member. FIG. 17 is a flow diagram of a method 1700 of evaluating a vessel according to some embodiments of the present disclosure. It is understood that additional steps can be provided before, during, and after the steps of method 1700, and some of the steps described can be replaced or eliminated for other embodiments of the method. The method 1700 allows operators to perform high-level measurements on a vessel and, based on the high-level measurements, to select vascular segments to measure further without necessarily relocating the sensing instrument. In block 1702, the sensing instrument, such as a flexible elongate member, is advanced into a vessel such that a sensing portion of the instrument extends through the region of the vessel to be imaged. The sensing portion may include any suitable medical sensors such as ultrasound transducers, pressure sensors, flow sensors, OCT transceivers, and/or other suitable sensors, and the associated sensors may correspond to one or more modalities including flow, optical flow, IVUS, photoacoustic IVUS, FL-IVUS, pressure, optical pressure, FFR determination, CFR determination, OCT, transesophageal echocardiography, image-guided therapy, other suitable modalities, and/or combinations thereof.

In block 1704, a first set of medical data measurements are obtained using a first subset of the plurality of sensors. The first set of medical data corresponds to a first modality such as flow, optical flow, IVUS, photoacoustic IVUS, FL-IVUS, pressure, optical pressure, FFR determination, CFR determination, OCT, transesophageal echocardiography, image-guided therapy, other suitable modalities, and/or combinations thereof. In block 1706, the first set of medical data is presented to a user via a display device. A representation of the vascular region is also presented via the display device. The representation may divide the region into a collection of selectable vascular segments where each segment has one or more sensors positioned to measure the segment. In some embodiments, the medical data is given context by displaying the medical data in conjunction with the vascular segments. In an embodiment where the set of medical data includes pressure data used to determine FFR ratios, each segment indicator is overlaid with an FFR ratio calculated for the segment. In a further embodiment where the set of medical data includes IVUS data, the IVUS data is overlaid with icons indicating the corresponding segments.

In some embodiments, presenting the first set of medical data includes highlighting an identified portion of the set of medical data. In an exemplary embodiment where the medical data includes pressure data used to determine FFR ratios, ratios less than a critical threshold and suggesting a potential stenosis are highlighted. In an exemplary embodiment where the medical data includes IVUS data, regions corresponding to a bifurcation, a stenosis, a plaque, a vascular dissection, a lesion, and/or a stent are highlighted.

The user may then select a segment of the vascular region to analyze in further detail. In block 1708, a user input specifying a segment is received. In block 1710, a second set of measurements is obtained using a second subset of sensors that includes the sensors positioned to measure the selected segment. Thus, the second set of measurement data measures the selected segment of the vascular region. Because the sensing instrument includes sensors arranged along the length of the sensing portion, the second set of measurements can be obtained without necessarily adjusting the position of the sensing portion. In some embodiments where the sensing instrument includes a variety of sensors arranged along the length, the second set of measurements corresponds to a different modality than the first set of measurements.

In some embodiments, additional vascular segments can be selected for further measurement without repositioning the sensing portion. In block 1712, a second user input specifying a second segment of the vessel region is received. In block 1714, a third set of measurements corresponding to the second selected segment is obtained. The third set of measurements is obtained without necessarily adjusting the position of the sensing portion.

Figure 18:
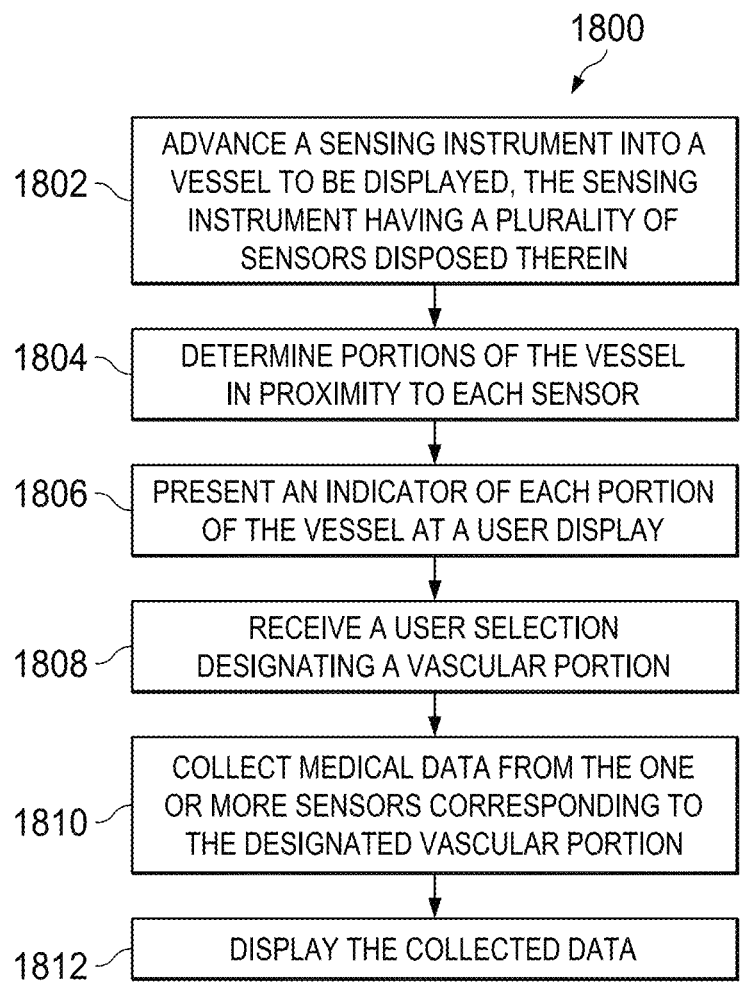
FIG. 18 is a flow diagram of a method of displaying medical data by simulating pullback of an intravascular sensing device according to some embodiments of the present disclosure.

Referring now to FIG. 18, in some embodiments, the user can obtain detailed measurements in a manner resembling a physical advance and pullback of a narrow-window sensing device. FIG. 18 is a flow diagram of a method 1800 of displaying medical data by simulating pullback of an intravascular sensing device according to some embodiments of the present disclosure. It is understood that additional steps can be provided before, during, and after the steps of method 1800, and some of the steps described can be replaced or eliminated for other embodiments of the method. The method 1800 allows users to perform a virtual pullback without necessarily moving the sensing device and without the delay and risk of lost alignment caused by physical movement. In block 1802, a sensing instrument, such as a flexible elongate member, having a plurality of sensors is advanced into a vessel to be displayed. The sensors may include any suitable medical sensors such as ultrasound transducers, pressure sensors, flow sensors, OCT transceivers, and/or other suitable sensors, and the associated sensors may correspond to one or more modalities including flow, optical flow, IVUS, photoacoustic IVUS, FL-IVUS, pressure, optical pressure, FFR determination, CFR determination, OCT, transesophageal echocardiography, image-guided therapy, other suitable modalities, and/or combinations thereof.

In block 1804, an imaging system divides the vessel into portions and determines one or more sensors positioned to measure each portion of the vessel. This may include collecting a preliminary set of medical data measurements as disclosed in block 1704 of FIG. 17. In block 1806, the system displays selectable indicators of each of the vascular portions via a user display. This may be substantially similar to the display disclosed in block 1706 of FIG. 17. In block 1808, the system receives a user selection designating a vascular portion. In block 1810, medical data is collected from the sensor or sensors positioned to measure the designated portion. This medical data may correspond to a different modality than the preliminary set of medical data. In block 1812, the medical data is displayed. The display of the medical data simulates a pullback of a sensing device without necessarily moving the sensing instrument.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. The processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of displaying a set of medical data by a medical imaging system, the method comprising:
  receiving a display attribute to be applied to a first data subset of the set of medical data independent of a second data subset of the set of medical data;
  receiving, by the medical imaging system, the set of medical data including the first data subset obtained using a first sensor based on the display attribute and the second data subset obtained using a second sensor, the first sensor and the second sensor being spaced from one another, wherein the display attribute designates a parameter of the first sensor specifying how, after processing the first data subset to generate an updated first data subset, the updated first data subset will be presented visually different than second data subset, wherein the first sensor comprises a first pressure sensor, the second sensor comprises a second pressure sensor, the updated first data subset comprises pressure ratio values determined based on pressure data obtained by the first pressure sensor, and the display attribute specifies one or more pressure ratio values that exceed a threshold value, and
  generating, by the medical imaging system, an instruction that affects the processing of the first data subset based on the display attribute;

providing the instruction for processing the first data subset;

receiving the updated first data subset, the updated first data subset being the result of processing the first data subset utilizing the provided instruction; and outputting, to a display device, a screen display that includes:
- a first representation of the updated first data subset, the displaying performed according to the display attribute, wherein the display attribute defines a visual appearance of the updated first data subset, wherein the first representation comprises:
  - the pressure ratio values; and
  - an indicator of the one or more pressure ratio values that exceed the threshold value; and
- a second representation of the second data subset independent of the display attribute, wherein the display attribute is applied only to the updated first data subset such that the updated first data subset is presented visually different than the second data subset as a result of the display attribute applied to the first data subset and not to the second data subset.

2. The method of claim 1, wherein outputting the screen display comprises outputting the first representation adjacent to the second representation.

3. The method of claim 1, wherein the first sensor and the second sensor are disposed on an elongate member of a medical sensing instrument.

4. The method of claim 3, wherein the first sensor and the second sensor are photoacoustic ultrasound transducers, and wherein the medical sensing instrument is a photoacoustic IVUS device.

5. The method of claim 3, wherein each of the first sensor and second sensor is one of a pressure sensor or a flow sensor.

6. The method of claim 3,
wherein the first sensor corresponds to a first modality;
wherein the second sensor corresponds to a second modality; and
wherein the first modality and the second modality are different.

7. The method of claim 1, further comprising:
receiving an additional display attribute to be applied to the second data subset of the set of medical data independent of the first data subset, wherein the additional display attribute designates a parameter of the second sensor specifying how, after processing the second data subset to generate an updated second data subset, the updated second data subset will be presented visually different than the second data subset, and wherein the additional display attribute defines a visual appearance of the updated first data subset.

8. The method of claim 7, wherein the additional display attribute designates a list of data subsets within the set of medical data to be displayed according to the additional display attribute, the list of data subsets including the first second data subset.

9. The method of claim 7, wherein the additional display attribute includes a value that depends on at least one of a user preference, an operative course of a medical procedure being performed, a medical facility at which the medical procedure is performed, patient information, the first data subset, the second data subset, a status indicator, or a sensor attribute.

10. The method of claim 7, wherein the additional display attribute includes at least one of a threshold value, a pseudo-color conversion scheme, and a display state from the group consisting of a shown state, a dimmed state, or a hidden state.

11. The method of claim 7, further comprising:
generating, by the medical imaging system, an instruction that affects collection of the second data subset, and not the first data subset, based on the additional display attribute; and
providing, to the second sensor, the instruction for collecting the second data subset.

12. The method of claim 11, wherein the additional display attribute includes an operating parameter for only the second sensor, and wherein the generating the instruction that affects the collection of the second data subset is based on the operating parameter for second first sensor.

13. The method of claim 7, wherein the additional display attribute specifies how the second data subset is to be obtained from anatomy using the second sensor.

14. The method of claim 7, wherein the additional display attribute specifies how the second data subset is to be processed differently than the second first data subset to generate an updated second data subset.

15. The method of claim 7, wherein:
the first sensor comprises an ultrasound transducer,
the second sensor comprises a pressure sensor,
the additional display attribute specifies an anatomical structure to which the additional display attribute applies,
providing the instruction comprises generating an indicator of a boundary of the anatomical structure, and
the second representation comprises:
an ultrasound image obtained by the ultrasound transducer; and
the indicator of the boundary of the anatomical structure overlaid on the ultrasound image.

* * * * *